United States Patent [19]

Pellacini et al.

[11] Patent Number: 5,994,539

[45] Date of Patent: *Nov. 30, 1999

[54] MERCAPTO ACYL AMINOACID DERIVATIVES ENDOWED WITH DUAL ACE-NEP INHIBITORY ACTIVITY, USEFUL IN THE TREATMENT OF CARDIOVASCULAR DISEASES

[75] Inventors: Franco Pellacini, Milan; Stefano Romagnano, Buccinasco; Gabriele Norcini, Vizzola Ticino; Francesco Santangelo; Mario Fantucci, both of Milan; Claudio Semeraro, Bresso, all of Italy

[73] Assignee: Zambon Group S.p.A., Milan, Italy

[*] Notice: This patent is subject to a terminal disclaimer.

[21] Appl. No.: 08/993,567

[22] Filed: Dec. 18, 1997

Related U.S. Application Data

[62] Division of application No. 08/774,298, Dec. 24, 1996, Pat. No. 5,760,241
[60] Provisional application No. 60/015,047, Apr. 9, 1996.

[30] Foreign Application Priority Data

Jan. 23, 1996 [EP] European Pat. Off. .. PCT/EP96/00251

[51] Int. Cl.⁶ ..................... C07D 277/24; C07D 277/26; A61K 31/10; A61K 38/05; C07C 327/32; C07C 323/41
[52] U.S. Cl. .......................... 544/224; 514/247; 514/256; 514/357; 514/365; 514/378; 514/439; 514/471; 514/513; 514/532; 514/534; 514/570; 544/335; 546/340; 546/342; 548/204; 548/240; 548/247; 549/76; 549/553; 558/254; 558/255; 560/16; 560/147; 560/153; 562/426; 562/556; 562/557
[58] Field of Search ..................................... 558/254, 255; 560/16, 147, 153; 562/426, 556, 557; 548/204, 240, 247; 546/340, 342; 544/224, 335; 549/76, 553; 514/247, 256, 357, 365, 378, 439, 471, 513, 532, 534, 576

[56] References Cited

U.S. PATENT DOCUMENTS

| | | | |
|---|---|---|---|
| 3,821,268 | 6/1974 | Diamond et al. | 558/254 X |
| 3,897,480 | 7/1975 | Mita et al. | 558/254 X |
| 4,108,886 | 8/1978 | Ondetti | 558/254 |
| 4,176,235 | 11/1979 | Ondetti et al. | 562/556 |
| 4,435,329 | 3/1984 | McEvoy et al. | 558/254 |
| 4,513,009 | 4/1985 | Roques et al. | 514/513 |
| 4,798,904 | 1/1989 | Delaney et al. | 558/254 |
| 5,208,255 | 5/1993 | Duhamel et al. | 514/513 |
| 5,414,017 | 5/1995 | Delaney et al. | 514/512 |
| 5,508,266 | 4/1996 | Fink | 514/19 |
| 5,612,371 | 3/1997 | Danvy et al. | 514/465 |
| 5,760,241 | 6/1998 | Santangelo et al. | 548/204 |

FOREIGN PATENT DOCUMENTS

94/17036  8/1994  WIPO ................... 558/254

*Primary Examiner*—Floyd D. Higel
*Attorney, Agent, or Firm*—Nikaido Marmelstein Murray & Oram LLP

[57] ABSTRACT

Compounds of formula $$R-(CH_2)_n-\overset{R_1}{\underset{|}{CH}}-CONH-\left(\overset{R_2}{\underset{|}{CH}}-CONH\right)_m\overset{*}{\underset{|}{CH}}-COOR_4 \atop CH_2-R_3 \quad (I)$$

wherein R, $R_1$, $R_2$, $R_3$, $R_4$, m and n have the meanings reported in the description, processes for their preparation and pharmaceutical compositions which contain them as active ingredients are described.

The compounds of formula I are endowed with a mixed ACE-inhibitory and NEP-inhibitory activity and are useful in the treatment of cardiovascular diseases.

33 Claims, No Drawings

MERCAPTO ACYL AMINOACID DERIVATIVES ENDOWED WITH DUAL ACE-NEP INHIBITORY ACTIVITY, USEFUL IN THE TREATMENT OF CARDIOVASCULAR DISEASES

This application is a divisional application of application Ser. No. 08/774,298, filed Dec. 24, 1996, now U.S. Pat. No. 5,760,241, which is a Continuation-In-Part of application Ser. No. 60/015,047 filed Apr. 9, 1996. These applications are herein incorporated by reference.

The present invention relates to thiol derivatives with metallopeptidase inhibitory activity and, more particularly, it relates to mercaptoacylamino derivatives useful in the treatment of cardiovascular diseases.

The pharmacologic interest towards the study of metallopeptidase inhibitory molecules derives from the role that said enzymes exert on the level of the cardiocirculatory system It is well-known, in fact, that compounds with angiotensin converting enzyme (ACE) inhibitory activity are mainly useful in the treatment of hypertension, heart failure and post-infarct in that they inhibit the formation of angiotensin II, a substance which increases the blood pressure.

Compounds with endothelin converting enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase (NEP) enzyme, also called enkephalinase, are useful as vasodilators in that the NEP enzyme is responsible for the inactivation, not only of endogenous enkephaline, but also of some natriuretic factors such as the atrial factor (ANF), a hormone secreted by heart which increases the vasodilation and, on the renal level, increases diuresis and natriuresis.

Therefore, even exerting their action on the cardiovascular system with different mechanisms of action, the compounds with metallopeptidase inhibitory activity are generally used, alone or in combination, in the treatment of hypertension, renal failure, congestive heart failure and ischemic cardiopathologies.

Among the metallopeptidase inhibitors having a mercaptoacylamino structure. Thiorphan [(DL-(3-mercapto-2-benzylpropanoyl)glycine], described for the first time by Roques et al. in Nature, Vol. 288, pages 286–288, (1980), and Captopril (The Merck Index, XI ed., No. 1773, page 267) are considered the parent compounds for NEP-inhibitors and ACE-inhibitors, respectively.

Other molecules with a mercaptonacylamino structure endowed with metallopeptidase inhibitory activity are described in the literature.

The U.S. Pat. No. 4,401,677 and U.S. Pat. No. 4,199,512 (both in the name of E. R. Squibb & Sons, Inc.) describe mercaptoalkanoyl amino acids endowed with enkephalinase inhibitory activity and ACE-inhibitory activity, respectively.

The European patent application No. 0 566 157 (Schering Corporation) describing mercaptoalkanoyl amino acids endowed with neutral metalloendopeptidase inhibitory activity.

The European patent application No. 0 419 327 (Société Civile Bioproject) describes amino acid derivatives endowed with enkephalinase and ACE inhibitory activity.

The European patent application No. 0 449 523 (E. R. Squibb & Sons, Inc.) describes mercapto or acylthio trifluoromethylamides with NEP-inhibitory activity.

The international patent application No. WO 93/08162 [Rhone-Poulenc Rorer S. A.—Institut National de la Santé et de la Recherche Medicale (INSERM)] describes β, β-disubstituted α-mercaptomethylpropionylamides endowed with a mixed ACE/NEP inhibitory activity.

Among the compounds described in the patent application No. WO 93/08162, the compound known with the abbreviation RB 105 [N-[2-(mercaptomethyl)-3-phenylbutanoyl]-L-alanine] is under study as mixed ACE/NEP inhibitor for the treatment of cardiovascular diseases [Fournié-Zaluski M. C. et al., Proc. Natl. Acad. Sci. USA, vol 91, pages 4072–4076, (1994)]. The European patent application No. 0 524 553 [Institut National de la Santé et de la Recherche Medical (INSERM)] describes acylmercaptoalkanyldipepitdes endowed with neutral endopeptidase and peptidyldipeptidase A inhibitory activity.

α-Mercaptoacyl dipeptides endowed with ACE-inhibitory and NEP-inhibitory activity are also described by S. S. Bhagwat et al. in Bioorganic & Medicinal Chemistry Letters, 7, 735–738, 1995.

In this last work that authors conclude that, while the presence of a biphenyl group confers an interesting mixed ACE/NEP-inhibitory activity at the molecules having an α-mercaptoacyl dipeptide structure, the substitution of the biphenyl group with groups such as α- or β-naphthyl causes a significant loss of activity.

Now we have found mercaptoacylamino derivatives which are endowed with a remarkable inhibitory activity on the angiotensin converting enzyme as well as on the neutral endopeptidase enzyme (mixed or dual ACE/NEP inhibitory activity) which makes them particularly useful in the cardiovascular therapy.

Therefore, object of the present invention are the compounds of formula

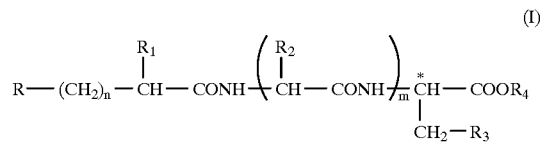

wherein

R is a mercapto group or a $R_5COS$ group convertible in the organism to mercapto group;

$R_1$ and $R_2$, the same or different, are a hydrogen atom, a straight or branched $C_1$–$C_6$ alkyl group, an aryl or an arylalkyl group having from 1 to 6 carbon atoms in the alkyl moiety wherein the aryl is a phenyl, a biphenyl, a naphthyl or a 5 or 6 membered aromatic heterocycle with one or two heteroatoms selected from the group consisting of nitrogen, oxygen and sulphur, wherein the aryl is optionally substituted with one or more substituents, the same or different, selected from the group consisting of halogen atoms, hydroxy groups, alkoxy, alkyl, alkylthio, alkylsulphonyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, amino-sulphonyl groups, mono- or di-alkylamino groups having from 1 to 6 carbon atoms in the alkyl moiety, and mono- or di-alkylaminocarbonyl groups having from 1 to 6 carbon atoms in the alkyl moiety;

$R_3$ is a phenyl group substituted by a phenyl or by a 5 or 6 membered aromatic heterocycle with 1 or 2 heteroatoms selected from the group consisting of nitrogen, oxygen and sulphur, said phenyl groups and heterocycle being optionally substituted with one or more substituents, the same or different, selected from the group consisting of halogen atoms, hydroxy groups, alkoxy, alkyl, alkylthio or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, and mono- or di-alkylaminocarbonyl groups having from 1 to 6 carbon atoms in the alkyl moiety;

$R_4$ is a hydrogen atom, a $C_1$–$C_4$ alkyl group or a benzyl group;

$R_5$ is a straight or branched $C_1$–$C_4$ alkyl group or a phenyl group;

m is 0 or 1;

n is 0 or 1;

the carbon atom marked with an asterisk is a stereogenic center;

and pharmaceutically acceptable salts thereof; with the proviso that when $R_3$ is a phenyl group substituted by a phenyl and $R_1$ is an arylalkyl group, the alkyl moiety of the arylalkyl group is a straight alkyl moiety.

The compounds of formula I contain at least a stereogenic center and can thus exist in the form of stereoisomers.

Therefore, object of the present invention are the compounds of formula I in the form of stereoisomeric mixture as well as in the form of single stereoisomers.

The compounds of formula I object of the present invention are endowed with a mixed ACE-inhibitory and NEP-inhibitory activity and are useful in the treatment of cardiovascular diseases.

In the present description, unless otherwise specified, with the term phenyl group substituted by a phenyl we intend a biphenyl group such as 2-phenyl, 3-biphenyl or 4-biphenyl group; with the term alkyl group we intend a straight or branched alkyl such as methyl, ethyl, n.propyl, isopropyl, n.butyl, sec-butyl, tert-butyl, isobutyl, n.pentyl, 2-pentyl, 3-pentyl, isopentyl, tert-pentyl, n.hexyl and isohexyl; with the term straight or branched alkoxy group we intend an alkoxy such as methoxy, ethoxy, n.propoxy and isopropxy group; with the term halogen atom we intend a fluorine, chlorine, bromine or iodine atom; with the term acyl we intend an acyl group deriving from an aliphatic or aromatic carboxylic acid such as acetic, propionic, butyric and benzoic acid; with the term aryl we intend an aromatic group such as phenyl, 2-biphenyl, 3-biphenyl, 4-biphenyl, 1-naphthyl and 2-naphthyl or a heterocyclic group containing one or two heteroatoms selected from the group consisting of nitrogen, oxygen and sulphur such as thiazole, isoxazole, oxazole, isothiazole, pyrazole, imidazole, thiophene, pyrrole, pyridine, pyrimidine, pyrazine, pyridazine and furan.

Examples of pharmaceutically acceptable salts of the compounds of formula I are the salts with alkali or alkaliearth metals and the salts with pharmaceutically acceptable organic bases or mineral acids.

A class of preferred compounds of formula I are the compounds wherein R is a mercapto group.

Another class of preferred compounds of formula I are the compounds wherein $R_1$ is an arylalkyl group optionally substituted with one or more substituents, the same or different, selected from the group consisting of halogen atoms, hydroxy groups, alkoxy and alkyl groups; having from 1 to 6 carbon atoms; $R_4$ is hydrogen and m is 0 and n is 1.

Another class of preferred compounds of formula I are the compounds wherein $R_3$ is a phenyl group para substituted by a phenyl or by a 5 or 6 membered aromatic heterocycle, said phenyl groups and heterocycle being optionally substituted as above indicated.

Still more preferred, in this class, are the compounds of formula I wherein $R_3$ is a phenyl group para substituted by a 5 or 6 membered aromatic heterocycle.

Still more preferred, in this latter class, are the compounds wherein R is a mercapto group. Another class of preferred compounds of formula I are the compounds wherein m is 0. More preferred, in this class, are the compounds wherein $R_3$ is a phenyl group para substituted by a phenyl or by a 5 or 6 membered aromatic heterocycle, said phenyl groups and heterocycle being optionally substituted as above indicated.

Still more preferred, in this class, are the compound of formula I wherein $R_3$ is a phenyl group para substituted by a 5 or 6 membered aromatic heterocycle and the compounds wherein R is a mercapto group.

Within the class of preferred compounds of formula I wherein m is 0, particularly preferred are the compounds wherein the carbon atom marked by an asterisk has the same absolute configuration as L-phenylalanine.

Within the aforementioned classes of preferred compounds of formula I, moreover, particularly preferred are the compounds wherein R3 is a phenyl group para substituted by a 5 or 6 membered aromatic heterocycle selected from the group consisting of thiazole, isoxazole, oxazole, isothiazole, pyrazole, imidazole, thiophene, pyrrole, pyridine, pyrimidine, pyrazine, pyridazine and furan.

Preferred examples of pharmaceutically acceptable salts of the compounds of formula I are the salts with alkali metals such as sodium, lithium and potassium and the salts with mineral acids such as hydrochloric and hydrobromic acid.

The compounds of formula I wherein R is a $R_5COS$ group convertible in the organism to mercapto group as well as the compounds of formula I wherein $R_4$ is a $C_1$–$C_4$ alkyl group or a benzyl group are biologic precursors (pro-drugs) of the corresponding compounds of formula I wherein R is a mercapto group (R=SH) or $R_4$ is a hydrogen atom ($R_4$=H), respectively.

Specific examples of preferred compound of formula I, object of the present invention, are:

N-[3-mercapto-2-phenylmethylpropionyl]-4-(2-thiazolyl)-L-phenylalanine;

N-[3-mercapto-2-phenylmethylpropionyl]-4-(2-furyl)-L-phenylalanine;

N-[3-mercapto-2-phenylmethylpropionyl]-4-(5-pyrimidinyl)-L-phenylalanine;

N-[3-mercapto-2-phenylmethylpropionyl]-4-(2-pyrazinyl)-L-phenylalanine;

N-[3-mercapto-2-phenylmethylpropionyl]-4-(3-pyridyl)-L-phenylalanine;

N-[3-mercapto-2-phenylmethylpropionyl]-4-(2-pyridyl)-L-phenylalanine;

N-[3-mercapto-2-phenylmethylpropionyl]-4-(2-thienyl)-L-phenylalanine;

N-[3-mercapto-2-phenylmethylpropionyl]-4-(3-thienyl)-L-phenylalanine;

N-[3-mercapto-2-phenylmethylpropionyl]-4-(3-furyl)-L-phenylalanine;

N-[3-mercapto-2-(3-pyrdidylmethyl)propionyl]-4-(2-thiazolyl)-L-phenylalanine;

N-[2-mercaptomethyl-3-phenylpropionyl]-(1,1'-biphenyl-4-yl)-L-alanine;

N-[2-mercaptomethyl-3-(3-methoxyphenyl)propionyl]-(1, 1'-biphenyl-1-yl)-L-alanine;

N-[2-mercaptomethyl-3-phenylpropionyl]-(3'-chloro-1,1'-biphenyl-4-yl)-L-alanine;

N-[2-isopropyl-3-mercaptopropionyl]-(1,1'-biphenyl-4-yl)-L-alanine;
N-[2-mercaptomethyl-3-(3-pyridyl)propionyl]-(1,1'-biphenyl-4-yl)-L-alanine;
N-[3-(2-furyl)-2-(mercaptomethyl)propionyl]-(1,1'-biphenyl-4-yl)-L-alanine;
N-[2-mercaptomethyl-3-(3-methyl-5-isoxazolyl)propionyl]-(1,1'-biphenyl-4-yl)-L-alanine;
N-(2-isobutyl-3-mercapto-propionyl)-4-(2-thiazolyl)-L-phenylalanine;
N-[3-mercapto-2-(3-methoxyphenyl)methyl-propionyl]-4-(2-thiazolyl)-L-phenylalanine;
N-[3-mercapto-2-(2-thienyl)methyl-propionyl]-4-(2-thiazolyl)-L-phenylalanine;
N [2-(2-fluorophenyl)methyl-3-mercapto-propionyl]-4-(2-thiazolyl)-L-phenylalanine;
N-[2-(2-furyl)methyl-3-mercapto-propionyl]-4-(2-thiazolyl)-L-phenylalanine;
N-[3-mercapto-2-(3-methyl-5-isoxazolyl)methyl-propionyl]-4-(2-thiazolyl)-L-phenylalanine;
the (2S) and (2R) stereoisomers and the prodrugs thereof.

The preparation of the compounds of formula I, object of the present invention, comprises the reaction between a compound of formula

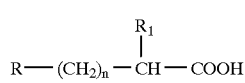
(II)

wherein
R, $R_1$ and n have the above reported meanings;
and a phenylalanine derivative of formula

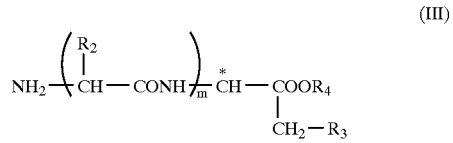
(III)

wherein
$R_2$, $R_3$, $R_4$ and m have the above reported meanings.

The condensation reaction is carried out according to conventional techniques of the chemistry of peptides.

Before carrying out the reaction, it can be useful to properly protect the eventual functional groups which could interfere in the reaction.

The optional protection is carried out according to conventional techniques.

In this respect, the compounds wherein R is a $R_5COS$ group are preferably used as intermediates of formula II, thus obtaining the corresponding compounds of formula I wherein R=$R_5COS$ from which, by hydrolysis, the compounds of formula I wherein R=SH can be obtained.

The evaluation of the usefulness of the optional protection as well as the selection of the kind of adopted protection, according to the reaction to be carried out and to the functional groups to be protected, are within the normal knowledge of the man skilled in the art.

The removal of the optional protective groups is carried out according to conventional techniques.

For a general reference to the use of protective groups in organic chemistry see Theodora W. Greene and Peter G. M. Wuts "Protective Groups in Organic Synthesis", John Wiley & Sons, Inc., II Ed., 1991.

The compounds of formula II are known compounds or easily prepared according to conventional methods.

For instance, the compounds of formula II can be prepared as reported in British patent No. 1,576,161 (E. R. Squibb & Sons Inc.) or, alternatively, according to the synthetic method described by M. C. Fournié-Zalusky et al. in J. Med. Chem. 1994, 37, 1070–1083.

Also the intermediates of formula III are known or easily prepared according to known methods.

For instance, the compounds of formula III can be prepared according to the synthetic methods described by Michel Sy et al. in Bull. Soc, Chim. Fr., 1276–1277, (1963), by Moses Lee et al. in J. Org. Chem, 1988, 53, 1855–1859 and by W. C. Shieh et al. in J. Org. Chem., 1992, 57, 379–381.

Alternatively, the compounds of formula III can be prepared by coupling methods (cross-coupling) starting from halogenated heterocyclic compounds and stannyl phenylalanine derivatives, as described by D. S. Wilbur et al. in Bioconjugate Chem., 1993, 4, 574–580.

The compounds of formula I in the form of single stereoisomers are prepared by stereoselective synthesis or by separation of the stereoisomeric mixture according to conventional techniques.

Also the preparation of the salts of the compounds of formula I, object of the invention, is carried out according to conventional techniques.

The compounds of formula I, object of the present invention, are endowed with a mixed or dual ACE-inhibitory and NEP-inhibitory activity and are useful in the treatment of cardiovascular diseases.

Althought both terms mixed and dual are indifferently used, the term dual is the one more commonly accepted in the literature for compounds endowed contemporaneously with ACE- and NEP-inhibitory activity.

In the present context, the terms mixed and dual are to be considered equivalent.

The inhibitory activity of the compounds of formula I was evaluated by means of in vitro tests in comparison to the aforementioned Thiorphan, Captopril and RB and by means of ex-vivo tests.

The in-vitro activity of the compounds of formula I, expressed as $IC_{50}$ (nM) value or as percentage of inhibition, is pharmacologically significant in comparison to the NEP-inhibitory activity of Thiorphan as well as in comparison to the ACE-inhibitory activity of Captopril. Furthermore, the in-vitro mixed ACE/NEP-inhibitory activity of the compounds of formula I, object of the present invention, is comparable or better than that of the mixed ACE/NEP inhibitor RB 105 (example 8). The mixed ACE/NEP-inhibitory activity of RB 105, however, was not confirmed by ex-vivo tests.

The ex-vivo inhibitory activity of the compounds of formula I, therefore, was evaluated in comparison to other known compounds (example 9).

In particular, N-[3-mercapto-2-(3,4-methylenedioxyphenyl)methyl-propionyl]-(S)-phenylalanine and N-[3-mercapto-2-(3,4-methylenedioxyphenyl)methyl-propionyl]-(S)-tyrosine, described as enkephalinase and ACE-inhibitors in the aforementioned European patent application No. 0419327 and hereinafter referred to as compounds R-1 and R-2 respectively, as well as N-(3-mercapto-2-methylpropanoyl)-L-tyrosine and N-(3-mercapto-2-methylpropanoyl)-L-triptophan, described as ACE-inhibitors in U.S. Pat. No. 4,199,512 and as enkephalinase inhibitors in U.S. Pat. No. 4,401,677 and hereinafter referred to as compounds R-3- and R-4 respectively, were used as comparison compounds.

The ex vivo ACE/NEP-inhibitory activity of the compounds of formula I, in particular, was evaluated by considering the enzymatic activity in tissue homogenates (lung and kidney for the ACE- and NEP-inhibitory activity, respectively) from spontaneously hypertensive rats (SHR), treated with the tested compounds by intravenous or oral route.

It is worth noting that the activity shown by the compounds of formula I in the ex-vivo test confirms the dual activity shown in the in-vitro test, also after oral administration.

Said activity, moreover, resulted to be significantly higher than that of the comparison compounds.

For a practical use in therapy, the compounds of formula I can be formulated in solid or liquid pharmaceutical compositions, suitable to oral or parenteral administration.

Therefore, the pharmaceutical compositions containing a therapeutically effective amount of a compound of formula I in admixture with a carrier for pharmaceutical use are a further object of the present invention.

Specific examples of pharmaceutical compositions according to the present invention are tablets, coated tablets, capsules, granulates, solutions and suspensions suitable to oral administration, solutions and suspensions suitable to parenteral administration.

The pharmaceutical compositions object of the present invention are prepared according to conventional techniques.

The daily dose of the compound of formula I or of the corresponding pro-drug will depend on different factors such as the seriousness of the disease, the individual response of the patient or the kind of formulation but it is usually comprised between 0.1 mg and 10 mg per kg of body weight of divided into a single dose or into two or more doses.

With the aim of illustrating the present invention, without limiting it, the following examples are now given.

Unless otherwise specified, the flash chromatographies were carried out by using flash chromatography silica gel from Baker company (code 7024-00) and the thin layer chromatographies (TLC) were carried out by using "silica gel plates $\alpha F_{254}$" from Merck company (code 1.05719).

EXAMPLE 1

Preparation of N-tert-butoxycarbonyl-4-(5-pyrimidinyl)-L-phenylalanine Ethyl Ester A mixture of 5-pyrimidinylboronic acid (850 mg; 2 mmoles), N-tert-butoxycarbonyl-4-trifluoromethylsulphonyl-L-phenylalanine ethyl ester (450 mg; 2.2 mmoles), a solution of sodium carbonate (530 mg) in water (2.59 ml) and a mixture of toluene:ethanol=10:45 (20 ml) was degassed with nitrogen for 30 minutes.

Subsequently, palladium(0)tetrakis(triphenylphosphine) (120 mg; 0.06 mmoles) was therein added and the reaction mixture was heated at 90° C. and kept under stirring for 3 hours.

The mixture was then kept at room temperature and N-tert-butoxycarbonyl-4-trifluoromethylsulphonyl-L-phenylalanine ethyl ester (112 mg) and palladium(O)tetrakis(triphenylphosphine) (30 mg) were added again.

The mixture was further heated at the temperature of 90° C. and kept under stirring for other 18 hours.

After cooling the reaction mixture at room temperature, ethyl acetate (100 ml) and water (40 ml) were added.

The phase were separated and the organic phase was dried on sodium sulphate and evaporated under vacuum. The obtained residue was purified by flash chromatography (silica gel, eluent hexane:ethyl acetate=7:3, pressure of nitrogen 0.1 atm) thus affording N-tert-butoxy-carbonyl-4-(5-pyrimidinyl)-L-phenylalanine ethyl ester (130 mg; 14% yield) as a colourless oil.

$^{1}$H-NMR (200 MHz, CDCl$_3$): δ (ppm): 1.24 (t, 3H, CH$_2$–CH$_3$); 1.40 [s, 9H, C(CH$_3$)$_3$]; 3.01–3.25 (m, 2H, CH$_2$-CH); 4.19 (q, 2H, CH$_2$–CH$_3$); 4.52–4.65 (m, 1H, CH-COO); 5.06 (d, 1H, NH); 7.25–7.52 (m, 4H, phenylene); 8.91 (s, 2H, N-CH-C-CH-N); 9.19 (s, 1H, N-CH-N).

EXAMPLE 2

Preparation of N-tert-butoxycarbonyl-4-(2-thiazolyl)-L-phenylalanine Methyl Ester N-tert-butoxycarbonyl-4-(trifluoromethylsulphonyl)-L-phenylalanine methyl ester (8 g; 32.3 mmoles) and palladium-bis(triphenylphosphine) chloride (2.3 g) were added to a solution of 2-trimethylstannyl-thiazole (13.8 g; 32.3 mmoles) in a mixture of tetrahydrofuran:toluene=10:1 (50 ml), previously degassed with nitrogen.

The mixture was refluxed for 24 hours and, subsequently, 2-trimethylstannyl-thiazole (2 g) was added again.

After 6 hours at reflux N-tert-butoxycarbonyl-4-(trifluoromethylsulphonyl)-L-phenylalanine methyl ester (2 g) and palladium-bis(triphenylphosphine) chloride (700 mg) were added.

The resultant reaction mixture was kept under stirring at 70° C. for 16 hours and, subsequently, cooled at room temperature.

Water (200 ml) was then added to the mixture which was extracted with methylene chloride (4×200 ml).

The collected organic phases were dried on sodium sulphate and evaporated under vacuum.

The obtained residue was purified by flash chromatography (silica gel, eluent methylene chloride:ethyl acetate=9:1, pressure of nitrogen=0.1 atm) thus affording N-tert-butoxycarbonyl-4-(2-thiazolyl)-L-phenylalanine methyl ester (2.3 g; 20% yield).

$^{1}$H-NMR (200 MHz, CDCl$_3$): δ (ppm): 1.40 [s, 9H, C(CH$_3$)$_3$]; 3.00–3.21 (m, 2H, CH$_2$); 3.70 (s, 3H, COOCH$_3$); 4.42–4.65 (m, 1H, CH-COO); 5.02 (bd, 1H, NH); 7.30 (d, 1H, S-CH-CH-N); 7.81 (d, 1H, S-CH-CH-N); 7.15–7.90 (m, 4H, phenylene).

EXAMPLE 3

Preparation of N-tert-butoxycarbonyl-4-(3-pyridyl)-L-phenylalanine Methyl Ester

3-Bromopyridine (1.67 g; 10 mmoles) and palladium(O) tetrakis(triphenylphosphine) (370 mg; 0.219 mmoles) were added to a solution of N-tert-butoxycarbonyl-4-(tributylstannyl)-L-phenylalanine methyl ester (4 g; 7.03 mmoles), prepared as described by D. S. Wilbur et al. in Bioconjugate Chem., 1973, 4, 574–580, in anhydrous dimethylformamide (30 ml), previously degassed with nitrogen.

The reaction mixture was kept under stirring for 10 minutes at room temperature and, subsequently, heated at 105° C. for 6 hours.

Palladium(O)tetrakis(triphenylphosphine) (0.035 mmoles) was again added and the mixture was kept under stirring at 105° C. for 8 hours and then cooled at room temperature.

Water (100 ml) was therein added and the reaction mixture was extracted with hexane (3×150 ml).

The collected organic phases were washed with a saturated aqueous solution of potassium fluoride, dried on sodium sulphate and evaporated under vacuum.

The obtained residue was collected with ethyl acetate and filtered.

The resultant solution was evaporated under vacuum and the residue was purified by flash chromatography (silica gel, eluent hexane:ethyl acetate=8:2, pressure of nitrogen 0.1 atm) affording N-tert-butoxycarbonyl-4-(3-pyridyl)-L-phenylalanine methyl ester (1.5 g; 60% yield) as a colourless oil.

Mass (C.I.):(M+H)$^+$=357

$^1$H-NMR (200 MHz, CDCl$_3$): δ (ppm): 1.40 [s, 9H, C(CH$_3$)$_3$]; 3.00–3.20 (m, 2H, CH$_2$); 3.71 (s, 3H, COOCH$_3$); 4.55 (m, 1H, CH-COO); 5.05 (bd, 1H, NH); 7.19–7.51 (m, 4H, phenylene); 7.30–8.82 (bm, 4H, pyridyl).

By working in an analogous way the following compounds were prepared:

N-tert-butoxycarbonyl-4-(2-pyridyl)-L-phenylalanine methyl ester

Mass (C.I.):(M+H)$^+$=357

$^1$H-NMR (200 MHz, CDCl$_3$): δ (ppm): 1.40 [s, 9H, C(CH$_3$)$_3$]; 3.03–3.21 (m, 2H, CH$_2$-CH); 3.70 (s, 3H, COOCH$_3$); 4.54–4.65 (m, 1H, CH-COO); 4.98 (d, 1H, CONH); 7.16–7.21 (m, 1H, N-C-CH-CH); 7.65–7.77 (m, 2H, N-CH-CH-CH); 7.19–7.93 (m, 4H, phenylene); 8.63–8.68 (m, 1H, N-CH);

N-tert-butoxycarbonyl-4(2-pyrazinyl)-L-phenylalanine methyl ester $^1$H-NMR (200 MHz, CDCl$_3$): δ (ppm): 1.40 [s, 9H, C(CH$_3$)$_3$]; 3.02 (m, 2H, CH$_2$); 3.70 (s, 3H, COOCH$_3$); 4.53–4.70 (m, 1H, CH-COO); 5.03 (bd, 1H, NH); 7.21–7.98 (m, 4H, phenylene); 8.49 and 8.62 [2(bs, 2H, N-CH-CH-N)]; 9.00 (s, 1H, CH-N-CH-CH);

N-tert-butoxycarbonyl-4-(2-thienyl)-L-phenylalanine methyl ester $^1$H-NMR (200 MHz, CDCl$_3$): δ (ppm): 1.4 [m, 9H, C(CH$_3$)$_3$]; 2.98–3.18 (m, 2H, CH$_2$); 3.71 (s, 3H, COOCH$_3$); 4.53–4.64 (m, 1H, CH-COO); 4.98 (bd, 1H, NH); 7.02–7.28 (m, 3H, thienyl); 7.10–7.54 (m, 4H, phenylene).

EXAMPLE 4

Preparation of 4-(3-pyridyl)-L-phenylalanine methyl ester dihydrochloride

Thionyl chloride (0.85 ml; 4.78 mmoles) was added dropwise to a solution of N-tert-butoxy-carbonyl-4-(3-pyridyl)-L-phenylalanine methyl ester (1.4 g; 3.93 mmoles) in methanol (30 ml), prepared as described in example 3, keeping the temperature at 0° C.

At the end of the addition, the reaction mixture was brought at room temperature and kept under stirring for 8 hours.

The solvent was then evaporated under vacuum affording 4-(3-pyridyl)-L-phenylalanine methyl ester dihydrochloride (820 mg; 71% yield) used as such in the following reactions.

Mass (C.I.):(M+H)$^+$=257 (free base)

$^1$H-NMR (200 MHz, D$_2$O): δ (ppm): 3.11–3.32 (m, 2H, CH$_2$); 3.67 (s, 3H, CH$_3$); 4.31–4.37 (m, 1H, CH); 7.30–7.63 (m, 4H, phenylene); 7.97 (dd, 1H, CH-N-CH-CH-CH); 8.59 (d, 1H, CH-N-CH-CH-CH); 8.65–8.71 (m, 1H, CH-N-CH-CH); 8.89 (d, 1H, CH-N-CH-CH-CH).

By working in an analogous way the following compounds were prepared:

4-(2-pyridyl)-L-phenylalanine methyl ester dihydrochloride

Mass (C.I.): (M+H)$^+$=257 (free base)

$^1$H-NMR (200 MHz, D$_2$O): δ (ppm): 3.12–3.33 (m, 2H, CH$_2$); 3.64 (s, 3H, CH$_3$); 4.30–4.37 (m, 1H, CH); 7.36–7.73 (m, 4H, phenylene); 7.78–8.58 (m, 4H, pyridyl);

4-(5-pyrimidinyl)-L-phenylalanine ethyl ester dihydrochloride $^1$H-NMR (200 MHz, DMSO-d$_6$): δ (ppm): 1.11 (t, 3H, CH$_2$-CH$_3$); 3.10–3.35 (m, 2H, CH$_2$-CH); 4.04–4.20 (m, 2H, CH$_2$-CH$_3$); 4.22–4.35 (m, 1H, CH); 7.40–7.84 (m, 4H, phenylene); 9.15 (s, 2H, N-CH-C-CH-N); 9.19 (s, 1H, N-CH-N);

4-(2-pyrazinyl)-L-phenylalanine methyl ester dihydrochloride

Mass (C.I.:(M+H)$^+$=258 (free base)

$^1$H-NMR (200 MHz, DCl 1N): δ (ppm): 3.45–3.67 (m, 2H, CH$_2$); 3.98 (s, 3H, CH$_3$); 4.65–4.72 (m, 1H, CH); 7.68–8.26 (m, 4H, phenylene); 9.02 (d, 1H, CH-N-CH-CH); 9.44 (dd, 1H, CH-N-CH-CH); 9.54 (d, 1H, CH-N-CH-CH);

4-(2-thienyl)-L-phenylalanine methyl ester hydrochloride

Mass (C.I.):(M+H)$^+$=262 (free base)

$^1$H-NMR (200 MHz, D$_2$O): δ (ppm): 2.98–3.19 (m, 2H, CH$_2$); 3.65 (s, 3H, CH$_3$); 4.21–4.28 (m, 1H, CH); 6.96–7.28 (m, 3H, thienyl); 7.08–7.52 (m, 4H, phenylene);

4-(2-thiazolyl)-L-phenylalanine methyl ester dihydrochloride $^1$H-NMR (200 MHz, D$_2$O): δ (ppm): 3.10–3.32 (m, 2H, CH$_2$-CH); 3.68 (s, 3H, CH$_3$); 4.30–4.38 (m, 1H, CH); 7.30–7.80 (m, 4H, phenylene); 7.70–7.91 (m, 2H, thiazolyl).

EXAMPLE 5

Preparation of 2-isobutyl-3-phenylcarbonylthio-propionic acid

A mixture of 2-isobutyl-acrylic acid (6.34 g; 49 mmoles) and thiobenzoic acid (5.96 ml; 51 mmoles) was heated at 100° C. under stirring for 2 hours.

The reaction mixture was then treated with petroleum ether 40–60° C. (100 ml) and cooled at −70° C. in a dry ice/acetone bath.

By filtration and washing with petroleum ether at −70° C. a residue was collected which, dried at reduced pressure, furnished 2-isobutyl-3-phenylcarbonylthio-propionic acid (11.12 g; 85% yield) as a white solide.

$^1$H-NMR (200 MHz, CDCl$_3$): δ (ppm); 0.90–1.00 (m, 6H); 1.40–1.90 (m, 3H); 2.70–2.90 (m, 1H); 3.10–3.40 (m, 2H); 7.35–7.62 (m, 3H); 7.90–8.00 (d, 2H).

By working in an analogous way the following compounds were prepared:

2-(3-methoxyphenyl)methyl-3-phenylcarbonylthio-propionic acid $^1$H-NMR (200 MHz, CDCl$_3$): δ (ppm): 2.32 (s, 3H); 2.80–3.15 (m, 5H); 3.77 (s, 3H); 6.70– 6.80 (m, 3H); 7.14–7.25 (m, 1H).

3-acetylthio-2-(2-fluorophenyl)methyl-propionic acid $^1$H-NMR (200 MHz, CDCl$_3$): δ (ppm): 2.31 (s, 3H); 2.90–3.20 (m, 5H); 6.95–7.30 (m, 4H).

3-phenylcarbonylthio-2-(2-thienyl)methyl-propionic acid benzylamine salt $^1$H-NMR (200 MHz, DMSO-d$_6$): δ (ppm): 2.45–3.25 (m, 5H, S-CH$_2$-CH-CH$_2$);3.90 (s, 2H, CH$_2$-phenyl); 6.85–7.91 (m, 13H, aryl).

EXAMPLE 6

Preparation of N-[(2S)-3-phenylcarbonylthio-2-phenylmethylpropionyl]-4-(2-thiazolyl)-L-phenylalanine Methyl Ester (Compound 1)

A solution of hydroxybenzotriazole (0.54 g; 4 mmoles) in tetrahydrofuran (30 ml) and, subsequently, a solution of dicyclohexylcarbodiimide (0.825 g; 4 mmoles) in methylene chloride (15 ml) were added, at 0° C. under stirring to a mixture of (2S)-3-phenylcarbonylthio-2-phenylmethylpropionic acid (1.2 g; 4 mmoles), 4-(2-thiazolyl)-L-phenylalanine methyl ester dihydrochloride (1.34 g; 4 mmoles), prepared as described in example 4, triethylamine (1.11 ml; 8 mmoles) in tetrahydrofuran (20 ml) and methylene chloride (30 ml).

The reaction mixture was kept under stirring for 20 hours, then dicyclohexyl urea was filtered off and the solvent was evaporated at reduced pressure.

The residue was collected with ethyl acetate and the solution was washed with an aqueous solution of sodium chloride at 20%, sodium bicarbonate at 5% and sodium chloride at 20% again.

After separation of the phases and evaporation of the organic phase, the resultant white solid was purified by flash chromatography (silica gel, eluent ethyl acetate:hexane=40:60, pressure of nitrogen 0.1 atm) thus affording N-[(2S)-3-phenylcarbonylthio-2-phenylmethylpropionyl]-4-(2-thiazolyl)-L-phenylalanine methyl ester (1.5 g).

m.p. 98–100° C.

Mass (C.I.):(M+H)$^+$=545

$^1$H-NMR (200 MHz, CDCl$_3$): δ (ppm): 2.63–3.35 (m, 7H, CH$_2$-CH-CH$_2$, CH$_2$-C$_6$H$_4$-thiazolyl); 3.68 (s, 3H, COOCH$_3$); 4.75–4.85 (m, 1H, CH-COO); 5.78 (d, 1H, NH); 7.10–8.00 (m, 16H, aryl).

By working in an analogous way, starting from known compounds or from the compounds prepared as described in examples 4 and 5, the following compounds were prepared:

N-[(2S)-3-phenylcarbonylthio-2-phenylmethylpropionyl]-4-(2-furyl)-L-phenylalanine methyl ester (compound 2)

m.p. 132–134° C.

Mass (C.I.)(M+H)$^+$=528

$^1$H-NMR (200 MHz, CDCl$_3$): δ (ppm): 2.60–3.35 (m, 7H, CH$_2$-CH-CH$_2$, CH$_2$-C$_6$H$_4$-furyl); 3.58 (s, 3H, COOCH$_3$); 4.71–4.81 (m, 1H, CH-COO); 5.73 (d, 1H, NH); 6.40–8.00 (m, 17H, aryl);

N-[(2S)-3-phenylcarbonylthio-2-phenylmethylpropionyl]-4-(5-pyrimidinyl)-L-phenylalanine ethyl ester (compound 3)

m.p. 117–119° C.

Mass (C.I.)(M+H)$^+$=554

$^1$H-NMR (200 MHz, CDCl$_3$): δ (ppm): 1.18 (t, 3H, CH$_3$-CH$_2$); 2.65–3.35 (m, 7H, CH$_2$-CH-CH$_2$, CH$_2$-C$_6$H$_4$-pyrimidinyl); 3.95–4.20 (m, 2H, COOCH$_2$); 4.70–4.80 (m, 1H, CH-COO); 5.78 (d, 1H, NH); 7.05–8.00 (m, 14H, phenyl, phenylene); 8.68 (s, 2H, CH-N-CH-N-CH); 9.11 (s, 1H, N-CH-N);

N-[(2S)-3-phenylcarbonylthio-2-phenylmethylpropionyl]-4-(2-pyrazinyl)-L-phenylalanine methyl ester (compound 4)

m.p. 145–147° C.

Mass (C.I.)(M+H)$^+$=540

$^1$H-NMR (200 MHz, CDCl$_3$): δ (ppm): 2.65–3.35 (m, 7H, CH$_2$-CH-CH$_2$, CH$_2$-C$_6$H$_4$-pyrazinyl); 3.61 (s, 3H, COOCH$_3$); 4.75–4.85 (m, 1H, CH-COO); 5.78 (d, 1H, NH); 7.10–8.00 (m, 14H, phenyl, phenylene); 8.48–8.75 (m, 3H, CH-N-CH-CH-N);

N-[(2S)-3-phenylcarbonylthio-2-phenylmethylpropionyl]-4-(3-pyridyl)-L-phenylalanine methyl ester (compound 5)

m.p. 132–134° C.

Mass (C.I.)(M+H)$^+$=539

$^1$H-NMR (200 MHz, CDCl$_3$): δ (ppm): 2.66–2.79 (m, 1H, CH$_2$-CH-CH$_2$); 2.88–3.35 (m, 6H, CH$_2$-CH-CH$_2$, CH$_2$-C$_6$H$_4$-pyridyl); 3.61 (s, 3H, COOCH$_3$); 4.75–4.85 (m, 1H, CH-COO); 5.77 (d, 1H, NH); 7.07–7.99 (m, 16H, CH-CH-CH-N, phenyl, phenylene); 8.51–8.64 (m, 2H, CH-N-CH);

N-[(2S)-3-phenylcarbonylthio-2-phenylmethylpropionyl]-4-(2-pyridyl)-L-phenylalanine methyl ester (compound 6)

m.p. 123–125° C.

Mass (C.I.)(M+H)$^+$=539

$^1$H-NMR (200 MHz, CDCl$_3$): δ (ppm): 2.63–2.77 (m, 1H, CH$_2$-CH-CH$_2$); 2.85–3.35 (m, 6H, CH$_2$-CH-CH$_2$, CH$_2$-C$_6$H$_4$-pyridyl); 3.56 (s, 3H, COOCH$_3$); 4.75–4.85 (m, 1H, CH-COO); 5.75 (d, 1H, NH); 7.09–7.99 (m, 16H, CH-CH-CH-N, phenyl, phenylene); 8.61–8.65 (m, 1H, N-CH-CH);

N-[(2S)-3-phenylcarbonylthio-2-phenylmethylpropionyl]-4-(2-thienyl)-L-phenylalanine methyl ester (compound 7)

Mass (C.I.)(M+H)$^+$=544

$^1$H-NMR (200 MHz, CDCl$_3$): δ (ppm): 2.64–3.36 (m, 7H, CH$_2$-CH-CH$_2$, CONH-CH-CH$_2$); 3.58 (s, 3H, COOCH$_3$); 4.74–4.83 (m, 1H, CH-COO); 5.74 (d, 1H, NH); 6.97–7.99 (m, 17H, aryl);

N-[(2S)-3-phenylcarbonylthio-2-phenylmethylpropionyl]-4-(3-thienyl)-L-phenylalanine methyl ester (compound 8)

Mass (C.I.)(M+H)$^+$=544

$^1$H-NMR (200 MHz, CDCl$_3$): δ (ppm): 2.63–3.35 (m, 7H, CH$_2$-CH-CH$_2$, NH-CH-CH$_2$); 3.58 (s, 3H, COOCH$_3$); 4.73–4.85 (m, 1H, CH-COO); 5.70–5.76 (bd, 1H, NH); 7.00–7.62 (m, 15H, phenyl, phenylene, CH-CH-S); 7.93–8.00 (m, 2H, CH-S-CH);

N-[(2S)-3-phenylcarbonylthio-2-phenylmethylpropionyl]-4-(3-furyl)-L-phenylalanine methyl ester (compound 9)

m.p. 115–117° C.

Mass (C.I.)(M+H)$^+$=528

$^1$H-NMR (200 MHz, CDCl$_3$): δ (ppm): 2.62–3.36 (m, 7H, CH$_2$-CH-CH$_2$, NH-CH-CH$_2$); 3.58 (s, 3H, COOCH$_3$); 4.71–4.82 (m, 1H, CH-COO); 5.72 (bd, 1H, NH); 6.50–8.00 (m, 17H, aryl);

N-[3-phenylcarbonylthio-2-(3-pyrdidylmethyl)propionyl]-4-(2-thiazolyl)-L-phenylalanine methyl ester—Stereoisomer A (compound 10)

Mass (C.I.)(M+H)$^+$=546

TLC (ethyl acetate:petroleum ether=95:5), Rf=0.33

$^1$H-NMR (200 MHz, CDCl$_3$): δ (ppm): 2.60–3.38 (m, 7H, CH$_2$-CH-CH$_2$, NH-CH-CH$_2$); 3.60 (s, 3H, COOCH$_3$); 4.79–4.90 (m, 1H, CH-COO); 6.21 (bd, 1H, NH); 7.29–7.81 (m, 2H, thiazolyl); 6.75–8.48 (m, 13H, phenyl, phenylene, pyridyl);

N-[3-phenylcarbonylthio-2-(3-pyridylmethyl)propionyl]-4-(2-thiazolyl)-L-phenylalanine methyl ester—Stereoisomer B (compound 11)

Mass (C.I)(M+H)$^+$=546

TLC (ethyl acetate:petroleum ether=95.5), Rf=0.24

$^1$H-NMR (200 MHz, CDCl$_3$): δ (ppm): 2.61–3.25 (m, 7H, CH$_2$-CH-CH$_2$, NH-CH-CH$_2$); 3.60 (s, 3H, COOCH$_3$); 4.80–4.91 (m, 1H, CH-COO); 6.09 (bd, 1H, NH); 7.27–7.80 (m, 2H, thiazoly); 7.10–8.40 (m, 13H, phenyl, phenylene, pyridyl);

N-[3-phenylcarbonylthio-2-(phenylmethyl)propionyl]-(1,1'-biphenyl-4-yl)-L-alanine phenyl methyl ester (compound 12)

m.p. 103–105° C.

$^1$H-NMR (200 MHz, CDCl$_3$): δ (ppm): 7.98-6.53 (m, 24H, 5Ar); 5.95-5.75 (2d, 1H, 2NH); 5.10-4.98 (m, 2H, COOCH$_2$); 4.95-4.78 (m, 1H, CHCOO); 3.35-2.60 (m, 7H, SCH$_2$CHCH$_2$ and CH$_2$-biphenyl).

[M-H]$^+$=613;

N-[2-acetylthiomethyl-3-(3-methoxyphenyl)propionyl]-(1,1'-biphenyl-4-yl)-L-alanine methyl ester—Stereoisomer A (compound 13)

m.p. 109–110° C.

TLC (ethyl acetate:hexane=30:70) R$_f$=0.18

$^1$H-NMR (200 MHz, CDCl$_3$): δ (ppm): 7.55–6.65 (m, 13H, 3Ar); 5.78 (d, 1H, NH); 4.85- 4.72 (m, 1H, CHCOO);

3.73 (s, 3H, OCH₃); 3.62 (s, 3H, COOCH₃); 3.20-2.71 (m, 6H, SCH₂CHCH₂ and CH₂-biphenyl); 2.63-2.49 (m, 1H, CH₂CHCH₂); 2.29 (s, 3H, CH₃COS) [M−H]⁺=506;
N-[2-acetylthiomethyl-3-(3-methoxyphenyl)propionyl]-(1,1'-biphenyl-4-yl)-L-alanine methyl ester—Stereoisomer B (compound 14)

m.p. 83–85° C.

TLC (ethyl acetate:hexane=30:70)R$_f$=0.17

¹H-NMR (200 MHz, CDCl₃): δ (ppm): 7.55-6.62 (m, 13H, 3Ar); 5.83 (d, 1H, NH); 4.91-4.81 (m, 1H, CHCOO); 3.77 (s, 3H, OCH₃); 3.68 (s, COOCH₃); 3.10-2.70 (m, 6H, SCH₂CHCH₂ and CH₂-biphenyl); 2.30 (s, 3H, CH₃COS)

[M−H]⁺=506;

N-[3-phenylcarbonylthio-2-(phenyl methyl)propionyl]-(3'-chloro-1,1'-biphenyl-4-yl)-L-alanine methyl ester (compound 15)

m.p. 111–113° C.

¹H-NMR (200 MHz, CDCl₃): δ (ppm): 8.00-6.62 (m, 18H, Ar); 5.89 and 5.71 (2d, 1H, NH); 4.91-4.75 (m, 1H, CHCOO); 3.60 (s, 3H, COOCH₃); 3.37-2.61 (m, 7H, CH₂CHCH₂ and CH₂-biphenyl)

[M−H]⁺=572

N-[(2S)-3-phenylcarbonylthio-2-(phenylmethyl)propionyl]-(1,1'-biphenyl-4-yl)-L-alanine methyl ester (compound 16)

M.P. 138–140° C.

TLC (ethyl acetate:hexane=3:7)R$_f$=0.25

¹H-NMR (200 MHz, CDCl₃): δ (ppm):8.00-7.01 (m, 19H, Ar); 5.75 (d, 1H, NH); 4.85-4.72 (m, 1H, CHCOO); 3.60 (s, 3H, COOCH₃); 3.35-2.61 (m, 7H, CH₂CHCH₂ and CH₂-biphenyl

[M−H]⁺=538;

N-[(2R)-3-phenylcarbonylthio-2-(phenyl methyl)propionyl]-(1,1'-biphenyl-4-yl)-L-alanine methyl ester (compound 17)

m.p. 156–158° C.

TLC (ethyl acetate:hexane=1:1)R$_f$=0.5

¹H-NMR (200 MHz, CDCl₃): δ (ppm): 7.98-6.61 (m, 19H, Ar); 5.89 (d, 1H, NH); 4.92-4.80 (m, 1H, CHCOO); 3.60 (s, 3H, COOCH₃); 3.30-2.60 (m, 7H, CH₂CHCH₂ and CH₂-biphenyl)

[M−H]⁺=538;

N-[2-isopropyl-3-(phenylcarbonylthio)propionyl]-(1,1'-biphenyl-4-yl)-L-alanine methyl ester (compound 18)

m.p. 123–125° C.

¹H-NMR (200 MHz, CDCl₃): δ (ppm): 7.98-7.07 (m, 14H, Ar); 5.93 (2d, 1H, NH); 5.02-4.87 (m, 1H, CHCOO); 3.71-3.65 (2s, 3H, COOCH₃); 3.51-3.00 (m, 4H, S-CH₂ and CH₂-biphenyl); 2.28-2.11 (m, 1H, CH-CONH); 2.82-2.02 (m, 1H, S-CH-CH-CH); 1.07 and 0.98 and 0.89 (3d, 6H, CH₃-CH-CH₃)

[M−H]⁺=490;

N-[2-phenylcarbonylthiomethyl-3-(3-pyridyl)propionyl]-(1,1'-biphenyl-4-yl)-L-alanine methyl ester—Stereoisomer A (compound 19)

m.p. 158–160° C.

TLC (methylene chloride:methanol=95:5)R$_f$=0.5

¹H-NMR (200 MHz, CDCl₃): δ (ppm): 8.40-6.75 (m, 18H, Ar); 6.98 (d, 1H, NH); 4.90-4.78 (m, 1H, CHCOO); 3.60 (s, 3H, COOCH₃); 3.35-2.65 (m, 7H, CH₂CHCH₂ and CH₂-biphenyl)

[M−H]⁺=539;

N-[2-phenylcarbonylthiomethyl-3-(3-pyridyl)propionyl]-(1,1'-biphenyl-4-yl)-L-alanine methyl ester—Stereoisomer B (compound 20)

m.p. 142–144° C.

TLC (methylene chloride:methanol=95:5)R$_f$=0.4

¹H, CHCOO); 3.60 (s, 3H, COOCH₃); 3.21-2.65 (m, 7H, CH₂CHCH₂ and CH₂-biphenyl)

[M−H]⁺=539;

N-[3-(2-furyl)-2-(phenylcarbonylthiomethyl)propionyl]-(1,1'-biphenyl-4-yl)-L-alanine methyl ester (compound 21)

m.p. 114–116° C.

¹H-NMR (200 MHz, CDCl₃): δ (ppm): 7.98-6.00 (m, 18H, Ar and NH); 4.95-4.82 (m, 1H, CHCOO); 3.69-3.62 (2s, 3H, COOCH₃); 3.36-2.35 (m, 7H, CH₂CHCH₂ and CH₂-biphenyl)

[M−H]⁺=528;

N-[3-(3-methyl-5-isoxazolyl)-2-(phenylcarbonylthiomethyl)propionyl]-(1,1'-biphenyl-4-yl)-L-alanine methyl ester—Stereoisomer A (compound 22)

m.p. 130–132° C.

TLC (ethyl acetate:hexane=1:1)R$_f$=0.39

¹H-NMR (200 MHz, CDCl₃): δ (ppm): 7.92-7.00 (m, 14H, Ar); 6.34 (d, 1H, NH; 5.88 (s, 1H, CH-isoxazolyl); 4.93-4.80 (m, 1H, CHCOO); 3.66 (s, 3H, COOCH₃); 3.40-2.80 (m, 7H CH₂CHCH₂ and CH₂-biphenyl)

[M−H]⁺=543;

N-[3-(3-methyl-5-isoxazolyl)-2(phenylcarbonylthiomethyl)propionyl]-(1,1'-biphenyl-4-yl)-L-alanine methyl ester—Stereoisomer B (compound 23)

m.p. 146–148° C.

TLC (ethyl acetate:hexane=1:1)R$_f$=0.34

¹H-NMR (200 MHz, CDCl₃): δ (ppm): 7.95-7.10 (m, 14H, Ar); 6.15 (d, 1H, NH); 5.91 (s, 1H, Ch-isoxazolyl); 4.95-4.85 (m, 1H, CHCOO); 3.70 (s, 3H, COOCH₃); 3.21-2.78 (m, 7H, CH₂CHCH₂ and CH₂-biphenyl

[M−H]⁺=543,

N-[(2S)-3-phenyl-2-(phenylcarbonylthio)propionyl]-(1,1'-biphenyl-4-yl)-L-alanine methyl ester (compound 24)

m.p. 128–130° C.

¹H-NMR (200 MHz, CDCl₃): δ (ppm): 7.82-7.00 (m, 19H, Ar); 6.70 (d, 1H, NH); 4.90-4.80 (m, 1H, CHCOO); 4.41 (t, 1H, CH-S); 3.70 (s, 3H, COOCH₃); 3.50-2.93 (m, 4H, CH₂CH-Ar and CH₂-biphenyl)

[M−H]⁺=524;

N-[2-isobutyl-3-phenylcarbonylthio-propionyl]-4-(2-thiazolyl)-L-phenylalanine methyl ester (compound 25)

¹H-NMR (200 MHz, CDCl₃): δ (ppm): 0.80-0.95 (m, 6H); 1.30-1.80 (m, 3H); 2.40-2.60 (m, 1H); 3.00–3.30 (m, 4H); 3.70 (d, 3H); 4.90-5.05 (m, 1H); 6.00–6.15 (bt, 1H); 7.10–8.00 (m, 11H);

N-[3-acetylthio-2-(3-methoxyphenyl)methyl-propionyl]-4-(2-thiazolyl)-L-phenylalanine methyl ester (compound 26)

¹H-NMR (200 MHz, CDCl₃): δ (ppm): 2.30 (d, 3H); 2.45–3.20 (m, 7H); 3.63 (d, 3H); 3.75 (d, 3H); 4.70–4.93 (m, 1H); 5.70–5.90 (dd, 1H); 6.60–6.85 (m, 4H); 7.17–7.32 (m, 3H); 7.68–7.90 (m, 3H);

N-[3-acetylthio-2-(3-fluorophenyl)methyl-propionyl]-4-(2-thiazolyl)-L-phenylalanine methyl ester (compound 27)

¹H-NMR (200 MHz, CDCl₃): δ (ppm): 2.29 (s, 3H); 2.55–3.20 (m, 7H); 3.65 (2s, 3H); 4.70–4.90 (m, 1H); 5.80–6.00 (2d, 1H); 6.70–7.32 (m, 3H);

N-[3-phenylcarbonylthio-2-(2-thienyl)methyl-propionyl]-4-(2-thiazolyl)-L-phenylalanine methyl ester (compound 28)

¹H-NMR (200 MHz, CDCl₃): δ (ppm): 2.68–3.37 (m, 7H); 3.60–3.61 (2s, 3H, COOCH₃); 4.31–4.45 (m, 1H, CH-COOCH₃); 6.01–6.10 (2d, 1H, NH); 6.80–8.00 (m, 14H).

EXAMPLE 7

Preparation of N-[(2S)-3-mercapto-2-phenylmethylpropionyl]-4-(2-thiazolyl)-L-phenylalanine (compound 29)

N-[(2S)-3-phenylcarbonylthio-2-phenylmethylpropionyl]-4-(2-thiazolyl)-L-phenylalanine methyl ester (1.4 g; 2.57 mmoles), prepared as described in example 6, was suspended in ethanol (30 ml), degassed by nitrogen bubbling to eliminate the oxygen.

An aqueous degassed solution of sodium hydroxide 1N (7.7 ml) and, at the end of the addition, further degassed ethanol (20 ml) were added dropwise at 5° C. to the suspension The reaction mixture was kept under stirring for 4 hours at room temperature, then cooled at 0° C. and acidified with hydrochloric acid 5% (10 ml).

The reaction mixture was evaporated to dryness and the residue was collected with acetonitrile and water and, subsequently, was filtered thus affording N-[(2S)-3-mercapto-2-phenylmethylpropionyl]-4(2-thiazolyl)-L-phenylalanine (1 g).

m.p. 180–182° C.

Mass (C.I.)(M+H)$^+$=427

$^1$H-NMR (200 MHz, DMSO-d$_6$): δ (ppm): 1.80–1.88 (m, 1H, SH); 2.22–2.84 (m, 5H, CH$_2$-CH-CH$_2$); 2.86–3.18 (m, 2H, CH$_2$-CH-COO); 4.46–4.57 (m, 1H, CH-COO); 7.10–7.25 (m, 5H, phenyl); 7.32–7.84 (m, 4H, phenylene); 7.74 (d, 1H, N-CH=CH-S); 7.89 (d, 1H, N-CH=CH-S); 8.35 (d, 1H, NH); 12.76 (s, 1H, COOH);

By working in an analogous way the following compounds were prepared:

N-[(2R)-3-mercapto-2-phenylmethylpropionyl]-4-(2-thiazolyl)-L-phenylalanine (compound 30)

$^1$H-NMR (200 MHz, DMSO-d$_6$): δ (ppm): 2.15–2.23 (m, 1H, SH); 2.31–2.74 (m, 5H, CH$_2$-CH-CH$_2$); 2.78–3.07 (m, 2H, CH$_2$-CH-COO); 4.42–4.53 (m, 1H, CH-COO); 7.02–7.80 (m, 9H, phenyl, phenylene); 7.75 (d, 1H, N-CH=CH-S); 7.90 (d, 1H, N-CH-S); 8.36 (d, 1H, NH);

N-[(2S)-3-mercapto-2-phenylmethylpropionyl]-4-(2-furyl)-L-phenylalanine (compound 31)

m.p. 153–155° C.

Mass (C.I)(M+H)$^+$=410

$^1$H-NMR (200 MHz, CDCl$_3$): δ (ppm): 1.40 (t, 1H, SH): 2.45–3.25 (m, 7H, CH$_2$-CH-CH$_2$, CH$_2$-CH-COO); 4.80–4.90 (m, 1H, CH-COO); 5.86 (d, 1H, NH); 6.42–7.42 (m, 3H, furyl); 7.07–7.57 (m, 9H, phenyl, phenylene);

N-[(2S)-3-mercapto-2-phenylmethylpropionyl]-4-(5-pyrimidinyl)-L-phenylalanine (compound 32)

m.p. 193–195° C.

Mass (C.I.)(M+H)$^+$=422

$^1$H-NMR (200 MHz, DMSO-d$_6$): δ (ppm): 1.81 (bm, 1H, SH); 2.21–3.20 (m, 7H, CH$_2$-CH-CH$_2$, CH$_2$-C$_6$H$_4$-pyrimidinyl); 4.46–4.57 (m, 1H, CH-COO); 7.06–7.29 (m, 5H, phenyl); 7.36–7.72 (m, 4H, phenylene); 8.33 (d, 1H, NHCO); 9.08 (s, 2H, N-CH-C-CH-N); 9.15 (s, 1H, N-CH-N);

N-[(2S)-3-mercapto-2-phenylmethylpropionyl]-4-(2-pyrazinyl)-L-phenylalanine (compound 33)

m.p. 176–178° C.

Mass (C.I.)(M+H)$^+$=422

$^1$H-NMR (200 MHz, DMSO-d$_6$): δ (ppm): 1.84 (bt, 1H, SH); 2.21–3.21 (m, 7H, CH$_2$-CH-CH$_2$, CH$_2$, CH$_2$-COO); 4.48–4.59 (m, 1H, CH-COO); 7.10–7.26 (m, 5H, phenyl); 7.37–8.05 (m, 4H, phenylene); 8.37 (d, 1H, NHCO); 8.58 (d, 1H, CH-N-CH-CH-N); 8.68–8.70 (m, 1H, CH-N-CH-CH-N); 9.21 (d, 1H, C-CH-N); 12.78 (b, 1H, COOH);

N-[(2S)-3-mercapto-2-phenylmethylpropionyl]-4-(3-pyridyl)-L-phenylalanine (compound 34)

m.p. 146–148° C.

Mass (C.I.)(M+H)$^+$=421

$^1$H-NMR (200 MHz, DMSO-d$_6$): δ (ppm): 1.69–1.89 (b, 1H, SH); 2.22–3.18 (m, 7H, CH$_2$-CH-CH$_2$, CH$_2$-phenylene); 4.45–4.56 (m, 1H, CH-COO); 7.09–7.26 (m, 5H, phenyl); 7.42–7.48 (m, 1H, CH-N-CH-CH-CH); 7.62–7.33 (m, 4H, phenylene); 7.98–8.04 (m, 1H, CH-N-CH-CH-CH); 8.30 (d, 1H, CONH); 8.53 (dd, 1H, CH-N-CH-CH-CH); 8.83 (d, 1H, CH-N-CH-CH-CH);

N-[(2S)-3-mercapto-2-phenylmethylpropionyl]-4-(2-pyridyl)-L-phenylalanine (compound 35)

m.p. 157–159° C.

Mass (C.I.)(M+H)$^+$=421

$^1$H-NMR (200 MHz, DMSO-d$_6$): δ (ppm): 1.87 (b, 1H, SH); 2.23–3.19 (m, 7H, S-CH$_2$-CH-CH$_2$, CONH-CH-CH$_2$); 4.44–4.45 (m, 1H, CH-COO); 7.09–7.93 (m, 8H, N-CH-CH-CH-CH, phenyl); 7.30–7.99 (m, 4H, phenylene); 8.29 (d, 1H, CONH); 8.61–8.65 (m, 1H, C-N-CH);

N-[(2S)-3-mercapto-2-phenylmethylpropionyl]-4-(2-thienyl)-L-phenylalanine (compound 36)

m.p. 152–154° C.

$^1$H-NMR (200 MHz, CDCl$_3$): δ (ppm): 1.34–1.43 (m, 1H, SH); 2.44–3.26 (m, 7H, S-CH$_2$-CH-CH$_2$, CONH-CH-CH$_2$); 4.80–4.89 (m, 1H, NH-CH-COO); 5.81 (d, 1H, NH); 7.02–7.52 (m, 12H, aryl);

N-[(2S)-3-mercapto-2-phenylmethylpropionyl]-4-(3-thienyl)-L-phenylalanine (compound 37)

m.p. 169–171° C.

Mass (C.I)(M+H)$^+$=426

TLC (ethyl acetate:hexane:acetic acid=50:50:5), Rf=0.44

$^1$H-NMR (200 MHz, CDCl$_3$): δ (ppm): 1.84 (bs, 1H, SH); 2.23–3.13 (m, 7H, S-CH$_2$-CH-CH$_2$, NH-CH-CH$_2$); 4.42–4.53 (m, 1H, NH-CH-COO); 7.12–7.80 (m, 12H, aryl); 8.30 (d, 1H, J$_{HH}$=8.2 Hz, NH);

N-[(2S)-3-mercapto-2-phenylmethylpropionyl]-4-(3-furyl)-L-phenylalanine (compound 38)

m.p. 140–142° C.

Mass (C.I)(M+H)$^+$=410

TLC (ethyl acetate:hexane:acetic acid=50:50:5), Rf=0.42

$^1$H-NMR (200 MHz, CDCl$_3$): δ (ppm): 1.79–1.90 (m, 1H, SH); 2.22–3.11 (m, 7H, S-CH$_2$-CH-CH$_2$, NH-CH-CH$_2$); 4.41–4.53 (m, 1H, NH-CH-COO); 7.11–7.50 (m, 9H, phenyl, phenylene); 6.91–8.12 (m, 3H, furyl); 8.30 (d, 1H, JHH=8.2 Hz, NH);

N-[3-pyridylmethyl)propionyl]-4-(2-thiazolyl)-L-phenylalanine Stereoisomer A (compound 39)

m.p. 193–196° C.

Mass (C.I.)(M+H)$^+$=428

TLC (methylene chloride:methanol:acetic acid=85:15:1.5), Rf=0.53

$^1$H-NMR (200 MHz, DMSO-d$_6$): δ (ppm): 2.37–3.05 (m, 7H, S-CH$_2$-CH-CH$_2$, NH-CH-CH$_2$); 4.36–4.47 (m, 1H, NH-CH-COO); 7.76–7.90 (m, 2H, thiazolyl); 7.10–8.33 (m, 9H, NH, pyridyl, phenylene);

N-[3-mercapto-2-(3-pyridylmethyl)propionyl]-4-(2-thiazolyl)-L-phenylalanine—Stereoisomer B (compound 40)

Mass (C.I.)(M+H)$^+$=428

TLC (methylene chloride:methanol:acetic acid=85:15:1.5), Rf=0.47

$^1$H-NMR (200 MHz, DMSO-d$_6$): δ (ppm): 2.28–3.20 (m, 7H, S-CH$_2$-CH-CH$_2$, NH-CH-CH$_2$); 4.20–4.35 (m, 1H, NH-CH-COO); 7.70–7.90 (m, 2H, thiazolyl); 7.17–8.40 (m, 9H, NH, pyridyl, phenylene);

N-(2-mercaptomethyl-3-phenylpropionyl)-(1,1'-biphenyl-4-yl)-L-alanine (compound 41)

m.p. 108–110° C.

$^1$H-NMR (200 MHz, CDCl$_3$): δ (ppm): 7.54-6.80 (m, 14H, Ar); 5.90 (d, 1H, J$_{HH}$=7.8 Hz, NH); 4.96-4.83 (m, 1H, CHCOO); 3.30-2.42 (m, 7H, SCH$_2$CHCH$_2$ and CH$_2$-biphenyl); 1.62-1.53 and 1.38-1.29 (m, 1H, SH).

[M–H]⁺=420;
N-[2-mercaptomethyl-3-(3-methoxyphenyl)propionyl]-(1,1'-biphenyl-4-yl)-L-alanine—Stereoisomer A (compound 42)

m.p. 122–124° C.
[α]$^{20}$=+55° (c=0.1; CHCl$_3$)
TLC(ethyl acetate:hexane:acetic acid=50:50:5)R$_f$=0.37
¹H-NMR (200 MHz, DMSO-d$_6$): δ (ppm): 8.31 (d, 1H, J$_{HH}$=8.1 Hz, NH); 7.62-6.69 (m, 13H, Ar); 4.56-4.45 (m, 1H, CHCOO); 3.69 (s, 3H, OCH$_3$); 3.17-2.20 (m, 7H, SCH$_2$CHCH$_2$ and CH$_2$-biphenyl); 1.84-1.72 (bs, 1H, SH) [M–H]⁺=450;

N-[2-mercaptomethyl-3-(3-methoxyphenyl)propionyl]-(1,1'-biphenyl-4-yl)-L-alanine—Stereoisomer B (compound 43)

m.p. 48–50° C.
[α]$^{20}$=+22.7° (c=0.1; CHCl$_3$)
¹H-NMR (200 MHz, DMSO-D$_6$): δ (ppm): 8.31 (d, 1H, J$_{HH}$=8.1 Hz, NH); 7.62-6.63 (m, 13H, Ar); 4.51-4.40 (m, 1H, CHCOO); 3.67 (s, 3H, OCH$_3$); 3.05-2.32 (m, 7H, SCH$_2$CHCH$_2$ and CH$_2$-biphenyl); 2.26-2.08 (bs, 1H, SH) [M–H]⁺=450;

N-(2-mercaptomethyl-3-phenylpropionyl)-(3'-chloro-1,1'-biphenyl-4-yl)-L-alanine—Stereoisomer A (compound 44)

¹H-NMR (200 MHz, CDCl$_3$): δ (ppm): 7.49-6.80 (m, 13H, Ar); 5.87 (d, 1H, J$_{HH}$=7.6 Hz, NH); 4.95-4.81 (m, 1H, CHCOO); 3.30-3.00 (m, 2H, CH$_2$-biphenyl); 2.94-2.43 (m, 5H, HS-CH$_2$-CH-CH$_2$); 1.38-1.29 (m, 1H, SH) [M–H]⁺=454;

N-(2-mercaptomethyl-3-phenylpropionyl)-(3'-chloro-1,1'-biphenyl-4-yl)-L-alanine—Stereoisomer B (compound 45)

¹H-NMR (200 MHz, CDCl$_3$): δ (ppm): 7.49-6.68 (m, 13H, Ar); 5.93 (d, 1H, J$_{HH}$=7.8 Hz, NH); 4.94-4.85 (m, 1H, CHCOO); 3.12-2.45 (m, 7H, CH$_2$-CH-CH$_2$ and CH$_2$-biphenyl); 1.61-1.52 (m, 1H, SH)

[M–H]⁺=454;

N-[(2S)-2-mercaptomethyl-3-phenylpropionyl]-(1,1'-biphenyl-4-yl)-L-alanine (compound 46)

m.p. 160–162° C.
¹H-NMR (200 MHz, CDCl$_3$): δ (ppm): 7.54-7.08 (m, 14H, Ar); 5.84 (d, 1H, J$_{HH}$=7.5 Hz, NH); 4.91-4.82 (m, 1H, CHCOO); 3.25 and 3.07 (ABX, Jab=14.1 Hz, Jax=5.4 Hz, Jbx=7.0 Hz, CH$_2$-biphenyl); 2.95-2.43 (m, 5H, HS-CH$_2$-CH-CH$_2$); 1.38-1.29 (m, 1H, SH) [M–H]⁺=420;

N-[(2R)-2-mercaptomethyl-3-phenylpropionyl]-(1,1'-biphenyl-4-yl)-L-alanine (compound 47)

m.p. 147–149° C.
¹H-NMR (200 MHz, CDCl$_3$): δ (ppm): 7.54-6.79 (m, 15H, Ar and COOH); 5.94 (d, 1H, J$_{HH}$=7.9 Hz, NH); 4.94-4.85 (m, 1H, CHCOO); 3.13-2.43 (m, 7H, HS-CH$_2$-CH-CH$_2$ and CH$_2$-biphenyl); 1.61-1.52 (m, 1H, SH)

[M–H]⁺=420;

N-[(2S)-2-mercapto-3-phenylpropionyl]-(1,1'-biphenyl-4-yl)-L-alanine (compound 48)

m.p. 93–95° C.
¹H-NMR (200 MHz, CDCl$_3$): δ (ppm): 8.82 (bs, 1H, COOH); 7.52-7.07 (m, 14H, Ar); 6.32 (d, 1H, J$_{HH}$=7.7 Hz, NH); 4.91-4.82 (m, 1H, CHCOO); 3.63-3.52 (m, 1H, Ch-SH; 3.26-3.02 (m, 4H, CH$_2$-biphenyl and CH$_2$-Ar); 1.91 (d, 1H, J$_{HH}$=9.0 Hz, SH) [M–H]⁺=406;

N-(2-isopropyl-3-mercaptopropionyl)-(1,1'-biphenyl-4-yl)-L-alanine (compound 49)

m.p. 182–184° C.
¹H-NMR (200 MHz, CDCl$_3$): δ (ppm): 7.56-7.27 (m, 9H, Ar); 6.10-6.05 (m, 1H, NH); 5.09-4.91 (m, 1H, CHCOO); 3.63-3.05 (m, 2H, CH$_2$-biphenyl); 2.86-2.45 (m, 2H, CH$_2$-SH); 2.02-1.92 (m, 1H, CH-CH$_2$-SH); 1.91-1.70 (m, 1H, CH$_3$-CH-CH$_3$); 1.60-1.21 (m, 1H, SH); 0.91-0.70 (m, 6H, CH$_3$-CH-CH$_3$)

[M–H]⁺=372;
N-[2-mercaptomethyl-3-(3-pyridyl)propionyl]-(1,1'-biphenyl-4-yl)-L-alanine hydrochloride—Stereoisomer A (compound 50)

¹H-NMR (200 MHz, DMSO-d$_6$): δ (ppm): 8.61-7.67 (m, 5H, pyridyl and CONH); 7.64-7.16 (m, 9H, biphenyl); 4.47-4.37 (m, 1H, CH-CH$_2$-biphenyl); 3.05-2.43 (m, 7H, CH$_2$-CH-CH$_2$ and CH$_2$-biphenyl); 2.26 (m, 1H, SH)
[M–H]⁺=121;

N-[2-mercaptomethyl-3-(3-pyridyl)propionyl]-(1,1'-biphenyl-4-yl)-L-alanine hydrochloride—Stereoisomer B (compound 51)

m.p. 215–217° C.
¹H-NMR (200 MHz, DMSO-d$_6$): δ (ppm): 8.74-7.85 (m, 5H, pyridyl and CONH); 7.61-7.28 (m, 9H, biphenyl); 4.54-4.42 (m, 1H, CH-CH$_2$-biphenyl); 3.13-2.37 (m, 7H, CH$_2$-CH-CH$_2$ and CH$_2$-biphenyl); 1.86 (m, 1H, SH)
[M–H]⁺=421;

N-[3-(2-furyl)-2-(mercaptomethyl)propionyl]-(1,1'-biphenyl-4-yl)-L-alanine (compound 52)

m.p. 137–140° C.
¹H-NMR (200 MHz, CDCl$_3$): δ (ppm): 7.56-7.08 (m, 10H, biphenyl and CH-O); 6.35 (b, 1H, COOH); 6.23-5.96 (m, 3H, CONH and O-CH-CH-CH); 5.00-4.87 (m, 1H, CH-CH$_2$-biphenyl); 3.33-2.43 (m, 7H, CH$_2$-CH-CH$_2$ and CH$_2$-biphenyl); 1.65-1.30 (m, 1H, SH) [M–H]⁺=410;

N-[2-mercaptomethyl-3-(3-methyl-5-isoxazolyl)propionyl]-(1,1'-biphenyl-4-yl)-L-alanine—Stereoisomer A (compound 53)

¹H-NMR (200 MHz, DMSO-d$_6$): δ (ppm): 12.82 (bs, 1H, COOH); 8.51 (d, 1H, J$_{HH}$=8.0 Hz, NH); 7.65–7.26 (m, 9H, biphenyl); 5.78 [s, 1H, CH(isoxazole)]; 4.53-4.42 (m, 1H, CH-COO); 3.14-2.43 (m, 7H, CH$_2$-CH-CH$_2$ and CH$_2$-biphenyl); 2.31 (bt, 1H, SH); 1.99 (s, 3H, CH$_3$-isoxazolyl);

N-[2-mercaptomethyl-3-(3-methyl-5-isoxazolyl)propionyl]-(1,1'-biphenyl-4-yl)-L-alanine—Stereoisomer B (compound 54)

m.p. 215–217° C.
¹H-NMR (200 MHz, DMSO-d$_6$): δ (ppm):12.81 (bs, 1H, COOH); 8.49 (d, 1H, J$_{HH}$=8.3 Hz, NH); 7.63-7.30 (m, 9H, biphenyl); 6.04 [s, 1H, CH(isoxazole)]; 4.59-4.48 (m, 1H, CH-COO); 3.18-2.33 (m, 7H, CH$_2$-CH-CH$_2$ and CH$_2$-biphenyl); 2.12 (s, 3H, CH$_3$-isoxazolyl); 1.86 (t, 1H, J$_{HH}$=8.5 Hz, SH);

N-(2-isobutyl-3-mercapto-propionyl)-4-(2-thiazolyl)-L-phenylalanine (compound 55)

Mass (C.I.)(M+H)⁺=393
¹H-NMR (200 MHz, DMSO-d$_6$): δ (ppm): 0.50-1.44 (m, 9H); 1.68-2.25(m, 4H); 2.79-3.22 (m, 2H); 4.50–4.63 (m, 1H); 7.34–7.85 (m, 4H); 7.73–7.90 (m, 2H); 8.27–8.39 (2d, 1H);

N-[3-mercapto-2-(3-methoxyphenyl)methyl-propionyl]-4-(2-thiazolyl)-L-phenylalanine (compound 56)

Mass (C.I.)(M+H)⁺=457
¹H-NMR (200 MHz, DMSO-d$_6$+D$_2$O): δ (ppm): 2.20–3.21 (m, 7H); 3.70 (d, 3H); 4.48 (m, 1H); 6.55–6.86 (m, 3H); 7.00–7.40 (m, 3H); 7.65–7.95 (m, 4H); 8.27–8.45 (bt, CONH);

N-[2-(2-fluorophenyl)methyl-3-mercapto-propionyl]-4-(2-thiazolyl)-L-phenylalanine (compound 57)

Mass (C.I.)(M+H)⁺=445
¹H-NMR (200 MHz, DMSO-$_6$): δ (ppm): 2.20–3.18 (m, 8H); 4.35–4.55 (m, 1H); 6.85–7.35 (m, 6H); 7.65–7.90 (m, 4H); 8.35 (d, 1H);

N-[3-mercapto-2-(2-thienyl)methyl-propionyl]-4-(2-thiazolyl)-L-phenylalanine (compound 58)

¹H-NMR (200 MHz, DMSO-d$_6$): δ (ppm): 1.82–3.19 (m, 8H, CH$_2$-CH$_2$-CH$_2$; NH-CH-CH$_2$); 4.44–4.59 (m, 1H, CH-COO); 6.62–7.91 (m, 9H, aryl);8.42 (d, 1H, NH);

N-[2-(2-furyl)methyl-3-mercapto-propionyl]-4-(2-thiazolyl)-L-phenylalanine (compound 59)

$^1$H-NMR (200 MHz, DMSO-d$_6$): δ (ppm): 1.79–3.18 (m, 8H, S-CH$_2$-CH$_2$-CH$_2$; NH-CH-CH$_2$); 4.43–4.58 (m, 4H, CH-NH); 5.79–7.47 (m, 3H, furyl);7.30–7.85 (m, 4H, phenylene); 7.73–7.91 (m, 2H, thiazolyl); 8.40–8.46 (2d, 1H, NH);

N-[3-mercapto-2-(3-methyl-5-isoxazolyl)methyl-propionyl]-4-(2-thiazolyl)-L-phenylalanine (compound 60)

$^1$H-NMR (200 MHz, DMSO-d$_6$): δ (ppm): 2.00 and 2.12 (2s, 3H, CH$_3$-isoxazolyl); 2.28–3.19 (m, 8H, S-CH$_2$-CH$_2$-CH$_2$; CH$_2$-phenylene); 4.43–4.59 (m, 1H, CH-NH); 5.75 and 6.03 (2s, 1H, isoxazolyl); 7.29–7.86 (m, 4H, phenylene); 7.74–7.90 (m, 2H, thiazolyl); 8.46–8.53 (2d, 1H, NH).

EXAMPLE 8

In vitro evaluation of the pharmacologic activity a) NEP-inhibitory activity

The NEP-inhibitory activity was evaluated in membranes from rat kidney cortex prepared according to the procedure described by T. Maeda et al. in Biochim. Biophys. Acta 1983, 731(1), 115–120.

By working at 0–4° C., kidneys were removed from male Sprague-Dawley rats weighing approximately 300 g.

Cortex was carefully dissected, finely minced and suspended in a homogenization buffer (10 mM sodium phosphate pH 7.4 containing 1 mM MgCl$_2$, 30 mM NaCl, 0.02% NaN$_3$) 1:15 weight/volume.

The tissue was then homogenized for 30 seconds using an Ultra-Turrax homogenizer. Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage. The membranes were stored in small aliquots at −80° C. until use.

The NEP-inhibitory activity was evaluated according to the method described by C. Llorens et al., in Eur. J. Pharmacol., 69, (1981), 113–116, as reported hereinafter.

Aliquots of the membrane suspension prepared as above described (concentration 5 μg/ml of proteins) were preincubated in the presence of an aminopeptidase inhibitor (Bestatin - 1 mM) for 10 minutes at 30° C.

[$^3$H][Leu$^5$]-enkephaline (15 nM) and buffer TRIS/HCl pH 7.4 (50 mM) were added in order to obtain a final volume of 100 μl.

Incubation (20 minutes at 30° C.) was stopped by adding HCl 0.1M (100 μl).

The formation of the metabolite [$^3$H]Tyr-Gly-Gly was quantified by chromatography on polystyrene columns (Porapak Q).

The inhibition of the metabolite formation in the membrane preparations treated with the compounds of formula I and with the comparative compounds with respect to the untreated membrane preparations was expressed as IC$_{50}$ (nM) value or as percentage of inhibition at a concentration corresponding to 10$^{-7}$M.

b) ACE-inhibitory activity

The ACE-inhibitory activity was evaluated according to the method reported in the literature by B. Holmquist et al., in Analytical Biochemistry 95, 540–548 (1979).

50 μM of ACE (250 mU/ml purified by lung rabbit, EC 3.4.15.1 SIGMA) were preincubated with 50 μl of the compound of formula I or of the comparison compound in thermostated cuvettes at 37° C.

The reaction was started by adding furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curves, the absorbance at 340 nm was recorded in continue for 5 minutes.

The percentage of the enzyme inhibition in the preparations treated with the compounds of formula I or with the comparative compounds with respect to the untreated preparations was expressed as IC$_{50}$ (nM) value.

As an example, we report in the following table 1 the IC$_{50}$ (nM) values or the percentages of inhibition (10$^{-7}$M) related to the ACE-inhibitory activity and NEP-inhibitory activity of the compounds 29, 31–38, 40–42, 46–47, 49–60 and of Thiorphan, Captopril and RB 105 as comparative compounds.

TABLE 1

ACE-inhibitory and NEP-inhibitory activity, expressed as IC$_{50}$ (nM) value or as percentage of inhibition (10$^{-7}$ M), of compounds 29, 31–38, 40–42, 46–47, 49–60, Thiorphan, Captopril and RB105.

| Compound | ACE-inhibitory activity IC$_{50}$ (nM) | NEP-inhibitory activity IC$_{50}$ (nM) | % inhibition (10$^{-7}$ M) |
|---|---|---|---|
| 29 | 3.2 | 1.8 | |
| 31 | 1.8 | 1.8 | |
| 32 | 1.9 | 1.8 | |
| 33 | 1.5 | 2.5 | |
| 34 | 1.7 | 2.6 | |
| 35 | 1.8 | 2.0 | |
| 36 | 1.6 | 0.6 | |
| 37 | 2.5 | 1.3 | |
| 38 | 2.4 | 1 | |
| 40 | 9.1 | 17.3 | |
| 41 | 5 | 5 | |
| 42 | 7.5 | 16 | |
| 46 | 2.6 | 1.8 | |
| 47 | 25.3 | 6.1 | |
| 49 | 3.8 | 1.2 | |
| 50 | 13 | 2.9 | |
| 51 | 2 | 13 | |
| 52 | 6 | 3.7 | |
| 53 | 13 | | 94% |
| 54 | 11 | | 76% |
| 55 | 5.8 | 1.8 | |
| 56 | 4.6 | 9.0 | |
| 57 | 10.7 | 11.2 | |
| 58 | 8.6 | 1.2 | |
| 59 | 8.6 | 4.0 | |
| 60 | 7.9 | 4.5 | |
| RB 105 | 5 | 24 | |
| Thiorphan | 99 | 11 | |
| Captopril | 3 | not active | |

The data reported in table 1 show that the compounds of formula I, object of the present invention, are endowed with a significant mixed ACE/NEP inhibitory activity.

Said activity is comparable to the ACE-inhibitory activity of Captopril as well as to the NEP-inhibitory activity of Thiorphan.

Furthermore, the mixed ACE/NEP-inhibitory activity of the compounds of formula I is comparable or better than that of the mixed ACE/NEP-inhibitor RB 105.

EXAMPLE 9

"Ex vivo" Evaluation of the Pharmacologic Activity a) NEP-inhibitory activity

The ex vivo NEP-inhibitory activity was evaluated according to the procedure reported in the literature by M. Orlowsky et al., in Biochemistry 1981, 20, 4942–4950.

The ACE-inhibitory activity of the tested compounds was expressed as percentage of ACE-inhibition in SHR lungs.

As an example, the percentages of basal enzymatic activity obtained in the ex vivo tests after the administration of compounds 29 and 41, as representative compounds of formula I, and of the comparison compounds R-1, R-2, R-3 and R-4 are reported in the following table 2.

TABLE 2

Percentages of ex vivo ACE-inhibition and NEP-inhibition, evaluated in lungs and kidneys of SHR respectively, of compounds 29 and 41 and of compounds R-1, R-2, R-3 and R-4

| Compound | Treatment | ACE-inhibition (lungs) | | NEP-inhibition (kidneys) | |
|---|---|---|---|---|---|
| | | 5 minutes | 60 minutes | 5 minutes | 60 minutes |
| 41 | i.v. (0.64 μmoles/kg) | 49% | | 20% | |
| 29 | i.v. (0.6 μmoles/kg) | 15% | | 34% | |
| 29 | i.v. (21 μmoles/kg) | 72% | | 49% | |
| 29 | oral (30 μmoles/kg) | | 36% | | 39% |
| | | 30 minutes | 4 hours | 30 minutes | 4 hours |
| 29 | oral (30 μmoles/kg) | 60% | 45% | 55% | 40% |
| R-1 | oral (30 μmoles/kg) | 25% | 20% | 5% | not active |
| R-2 | oral (30 μmoles/kg) | 30% | 25% | 30% | not active |
| R-3 | oral (30 μmoles/kg) | 25% | 20% | 10% | 5% |
| R-4 | oral (30 μmoles/kg) | 25% | 10% | not active | not active |

The inhibitory activity of the compounds of formula I was evaluated in kidneys of spontaneously hypertensive rats (SHR), 5 minutes after i.v. injection (0.6, 0.64 and 21 μmoles/kg) and 30 minutes, 60 minutes and 4 hours after oral administration (30 μmoles/kg) of the tested compounds.

After the removal of the kidneys from SHR, the renal tissue was homogenized and incubated for 15 minutes at 37° C. in the presence of Glutaryl-Ala-Ala-Phe-2-naphthylamide (GAAP), as a substrate, and aminopeptidase M at pH 7.6.

The reaction was stopped by adding an aqueous solution at 10% of trichloroacetic acid. The released 2-naphthylamine was determined by adding fast garnet dye (2 ml). Enzyme reaction rates were determined by measuring the increase in the optical density at 524 nm ($OD_{524}$) with respect to a standard obtained with 2-naphthylamine complexed with fast garnet.

The NEP-inhibitory activity of the tested compounds was expressed as percentage of NEP-inhibition in SHR kidneys.

b) ACE-inhibitory activity

The ex vivo ACE-inhibitory activity was evaluated by using a radiometric assay method, as reported in the literature by J. W. Ryan et al. in Biochem. J. (1977), 167, 501–504. The inhibitory activity of the compounds of formula I was evaluated in lungs of spontaneously hypertensive rats (SHR), 5 minutes after i.v. injection (0.6, 0.64 and 21 μmoles/kg) and 30 minutes, 60 minutes and 4 hours after oral administration (30 μmoles/kg) of the tested compounds.

After the removal of the lungs from SHR, the lung tissue was homogenized and incubated for 2 hours at 37° C. in the presence of [$^3$H]Hyp-Gly-Gly, as a substrate.

The reaction was stopped by adding hydrochloric acid.

The released radiolabelled hyppuric acid was extracted with ethyl acetate and counted by liquid scintillation spectrometry, according to conventional methods.

The data reported in table 2 confirm that the compounds of formula I, object of the present invention, are endowed with a significant dual ACE/NEP-inhibitory activity after intravenous administration as well as after oral administration.

The ex-vivo ACE/NEP-inhibitory activity of the compounds of formula I, moreover, results to be significantly higher than that of the comparison compounds.

What we claim is:

1. A compound of formula

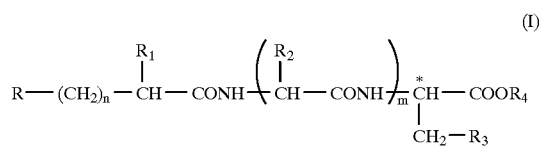

wherein

R is a mercapto group or a $R_5COS$ group wherein $R_5$ is a straight or branched $C_1$–$C_4$ alkyl group or a phenyl group, $R_1$ and $R_2$, the same or different, are a hydrogen atom, a straight or branched $C_1$–$C_6$ alkyl group, an aryl or an arylalkyl group having from 1 to 6 carbon atoms in the alkyl moiety wherein the aryl is a phenyl, a biphenyl, a naphthyl or a 5 or 6 membered aromatic heterocycle with one or two heteroatoms selected from the group consisting of nitrogen, oxygen and sulphur, wherein the aryl is unsubstituted or substituted with one or more substituents, the same or different, selected from the group consisting of halogen atoms, hydroxy groups, alkoxy, alkyl, alkylthio, alkylsulphonyl or alkoxycarbonyl groups having from 1 to 6 carbon atoms in the alkyl moiety, $C_1$–$C_3$ alkyl groups substituted by one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, and mono- or di-alkylaminocarbonyl groups having from 1 to 6 carbon atoms in the alkyl moiety; $R_3$ is a phenyl group substituted by a phenyl or by a 5 or 6 membered aromatic heterocycle with one or two heteroatoms selected from the group consisting of nitrogen, oxygen and sulphur, said phenyl groups and heterocycle being unsubstituted or substituted with one or more substituents, the same or different, selected from the group consisting of halogen atoms, hydroxy groups, alkoxy, alkyl, alkylthio or alkoxycarbonyl groups having from 1 to 6 carbon atoms in the alkyl moiety, $C_1$–$C_3$ alkyl groups substituted by one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, and mono- or di-alkylaminocarbonyl groups having from 1 to 6 carbon atoms in the alkyl moiety;

$R_4$ is a hydrogen atom, a $C_1$–$C_4$ alkyl group or a benzyl group;

m is 0 or 1;

n is 0 or 1;

the carbon atom marked with an asterisk is a stereogenic center; or its pharmaceutically acceptable salts;

with the proviso that when $R_3$ is a phenyl group substituted by a phenyl and $R_1$ is an arylalkyl group, the alkyl moiety of the arylalkyl group is a straight alkyl moiety excluding.

2. A compound according to claim 1 wherein m is 0.

3. A compound according to claim 2 wherein n is 1.

4. A compound according to claim 1 wherein $R_1$ is an arylalkyl group optionally substituted with one or more substitutents, the same or different, selected from the group consisting of halogen atoms, hydroxy groups, alkoxy and alkyl groups, having from 1 to 6 carbon atoms;

$R_4$ is hydrogen and m is 0 and n is 1.

5. A compound according to claim 1 wherein $R_3$ is a phenyl group para substituted by a phenyl or by a 5 or 6 membered aromatic heterocycle with one or two heteroatoms selected from the group consisting of nitrogen, oxygen and sulphur, said phenyl groups and heterocycle being optionally substituted with one or more substituents, the same or different, selected from the group consisting of halogen atoms, hydroxy groups, alkoxy, alkyl, alkylthio or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, non- or di-alkylamino groups having from 1 to 6 carbon atoms in the alkyl moiety, and mono- or di-alkylaminocarbonyl groups having from 1 to 6 carbon atoms in the alkyl moiety.

6. A compound according to claim 5 wherein $R_3$ is a phenyl group para substituted by a phenyl group, said phenyl groups being optionally substituted as in claim 5.

7. A compound according to claim 5 wherein $R_3$ is a phenyl group para substituted by a 5 or 6 membered aromatic heterocycle with one or two heteroatoms selected from the group consisting of nitrogen, oxygen and sulphur.

8. A compound according to claim 2 wherein $R_3$ is a phenyl group para substituted by a phenyl or by a 5 or 6 membered aromatic heterocycle with one or two heteroatoms selected from the group consisting of nitrogen, oxygen and sulphur, said phenyl groups and heterocycle being unsubstituted or substituted with one or more substituents, the same or different, selected from the group consisting of halogen atoms, hydroxy groups, alkoxy, alkyl, alkylthio or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, and mono-or di-alkylaminocarbonyl groups having from 1 to 6 carbon atoms in the alkyl moiety.

9. A compound according to claim 8 wherein $R_3$ is a phenyl group para substituted by a phenyl group, said phenyl groups being optionally substituted as in claim 8.

10. A compound according to claim 8 wherein $R_3$ is a phenyl group para substituted by a 5 or 6 membered aromatic heterocycle with one or two heteroatoms selected from the group consisting of nitrogen, oxygen and sulphur, said phenyl and heterocycle being optionally substituted as in claim 8.

11. A compound according to claim 7 wherein the aromatic heterocycle is selected from the group consisting of thiazole, isoxazole, oxazole, isothiazole, pyrazole, imidazole, thiophene, pyrrole, pyridine, pyrimidine, pyrazine, pyridazine and furan.

12. A compound according to claim 10 wherein the aromatic heterocycle is selected from the group consisting of thiazole, isoxazole, oxazole, isothiazole, pyrazole, imidazole, thiophene, pyrrole, pyridine, pyrimidine, pyrazine, pyridazine and furan.

13. A compound according to claim 1 wherein R is a mercapto group.

14. A compound according to claim 5 wherein R is a mercapto group.

15. A compound according to claim 7 wherein R is a mercapto group.

16. A compound according to claim 8 wherein R is a mercapto group.

17. A compound according to claim 10 wherein R is a mercapto group.

18. A process for the preparation of a compound of formula

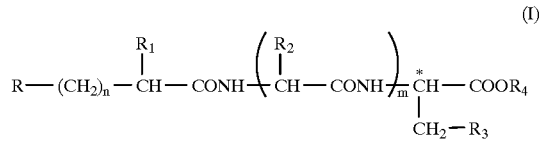

(I)

wherein R, $R_1$, $R_2$, $R_3$, $R_4$, m and n have the meanings reported in claim 1, which comprises the reaction between a compound of formula

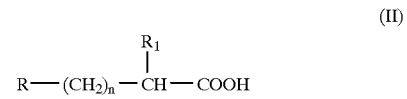

(II)

wherein

R, $R_1$ and n have the meanings reported in claim 1;

and a phenylalanine derivative of formula

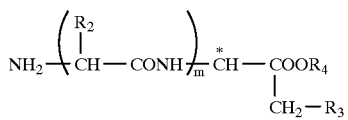

wherein $R_2$, $R_3$, $R_4$ and m have the meanings reported in claim 1.

19. A process according to claim 18 wherein m is 0.

20. A pharmaceutical composition containing a therapeutically effective amount of a compound according to claim 1 in admixture with a carrier for pharmaceutical use.

21. A pharmaceutical composition according to claim 20 for the treatment of a cardiovascular disease.

22. A method for the treatment of a cardiovascular disease comprising the administration of a therapeutically effective amount of a compound according to claim 1.

23. A method for the treatment of a cardiovascular disease comprising the administration of a dual ACE- and NEP-inhibiting amount of a compound according to claim 1.

24. A method for the treatment of a cardiovascular disease comprising the administration of an ACE-inhibiting amount of a compound according to claim 1.

25. A method for the treatment of a cardiovascular disease comprising the administration of a NEP-inhibiting amount of a compound according to claim 1.

26. A compound according to claim 1 wherein m is 0 and the carbon atom marked by an asterisk in formula I has the same absolute configuration as L-phenylalanine.

27. A compound according to claim 26 selected from the group consisting of:

N-[(2S)-3-phenylcarbonylthio-2-phenylmethylpropionyl]-4-(2-thiazolyl)-L-phenylalanine methyl ester;

N-[(2S)-3-phenylcarbonylthio-2-phenylmethylpropionyl]-4-(2-furyl)-L-phenylalanine methyl ester;

N-[(2S)-3-phenylcarbonylthio-2-phenylmethylpropionyl]-4-(5-pyrimidinyl)-L-phenylalanine ethyl ester;

N-[(2S)-3-phenylcarbonylthio-2-phenylmethylpropionyl]-4-(2-pyrazinyl)-L-phenylalanine methyl ester;

N-[(2S)-3-phenylcarbonylthio-2-phenylmethylpropionyl]-4-(3-pyridyl)-L-phenylalanine methyl ester;

N-[(2S)-3-phenylcarbonylthio-2-phenylmethylpropionyl]-4-(2-pyridyl)-L-phenylalanine methyl ester;

N-[(2S)-3-phenylcarbonylthio-2-phenylmethylpropionyl]-4-(2-thienyl)-L-phenylalanine methyl ester;

N-[(2S)-3-phenylcarbonylthio-2-phenylmethylpropionyl]-4-(3-thienyl)-L-phenylalanine methyl ester;

N-[(2S)-3-phenylcarbonylthio-2-phenylmethylpropionyl]-4-(3-furyl)-L-phenylalanine methyl ester;

N-[3-phenylcarbonylthio-2-(3-pyridylmethyl)propionyl]-4-(2-thiazolyl)-L-phenylalanine methyl ester;

N-[3-phenylcarbonylthio-2-(phenylmethyl)propionyl]-(1,1'-biphenyl-4-yl)-L-alanine phenylmethyl ester;

N-[2-acetylthiomethyl-3-(3-methoxyphenyl)propionyl]-(1,1'-biphenyl-4-yl)-L-alanine methyl ester;

N-[3-phenylcarbonylthio-2-(phenylmethyl)propionyl]-3'-chloro-1,1'-biphenyl-4-yl)-L-alanine methyl ester;

N-[(2S)-3-phenylcarbonylthio-2-(phenylmethyl)propionyl]-(1,1'-biphenyl-4-yl)-L-alanine methyl ester;

N-[(2R)-3-phenylcarbonylthio-2-(phenylmethyl)propionyl]-(1,1'-biphenyl-4-yl)-L-alanine methyl ester;

N-[2-isopropyl-3-(phenylcarbonylthio)propionyl]-(1,1'-biphenyl-4-yl)-L-alanine methyl ester;

N-[2-phenylcarbonylthiomethyl-3-(3-pyridyl)propionyl]-(1,1'-biphenyl-4-yl)-L-alanine methyl ester;

N-[3-(2-furyl)-2-(phenylcarbonylthiomethyl)propionyl]-(1,1'-biphenyl-4-yl)-L-alanine methyl ester;

N-[3-(3-methyl-5-isoxazolyl)-2-(phenylcarbonylthiomethyl)propionyl]-(1,1'-biphenyl-4-yl)-L-alanine methyl ester;

N-[(2S)-3-phenyl-2-(phenylcarbonylthio)propionyl]-(1,1'-biphenyl-4-yl)-L-alanine methyl ester;

N-(2-isobutyl-3-phenylcarbonylthio-propionyl)-4-(2-thiazolyl)-L-phenylalanine methyl ester;

N-[3-acetylthio-2-(3-methoxyphenyl)methyl-propionyl]-4-(2-thiazolyl)-L-phenylalanine methyl ester;

N-[3-acetylthio-2-(2-fluorophenyl)methyl-propionyl]-L-phenylalanine methyl ester;

N-[3-phenylcarbonylthio-2-(2-thienyl)methyl-propionyl]-4-(2-thiazolyl)-L-phenylalanine methyl ester;

N-[(2S)-3-mercapto-2-phenylmethylpropionyl]-4-(2-furyl)-L-phenylalanine;

N-[(2S)-3-mercapto-2-phenylmethylpropionyl]-4-(5-pyrimidinyl)-L-phenylalanine;

N-[(2S)-3-mercapto-2-phenylmethylpropionyl]-4-(2-pyrazinyl)-L-phenylalanine;

N-[(2S)-3-mercapto-2-phenylmethylpropionyl]-4-(3-pyridyl)-L-phenylalanine;

N-[(2S)-3-mercapto-2-phenylmethylpropionyl]-4-(2-pyridyl)-L-phenylalanine;

N-[(2S)-3-mercapto-2-phenylmethylpropionyl]-4-(2-thienyl)-L-phenylalanine;

N-[(2S)-3-mercapto-2-phenylmethylpropionyl]-4-(3-thienyl)-L-phenylalanine;

N-[(2S)-3-mercapto-2-phenylmethylpropionyl]-4-(3-furyl)-L-phenylalanine;

N-[3-mercapto-2-(3-pyridylmethyl)propionyl]-4-(2-thiazolyl)-L-phenylalanine;

N-(2-mercaptomethyl-3-phenylpropionyl)-(1,1'-biphenyl-1-yl)-L-alanine;

N-[2-mercaptomethyl-3-(3-methoxyphenyl)propionyl]-(1,1'-biphenyl-4-yl)-L-alanine;

N-(2-mercaptomethyl-3-phenylpropionyl)-(3'-chloro-1,1'-biphenyl-4-yl)-L-alanine;

N-[(2S)-2-mercaptomethyl-3-phenylpropionyl]-(1,1'-biphenyl-4-yl)-L-alanine;

N-[(2S)-2-mercaptomethyl-3-phenylpropionyl]-(1,1'-biphenyl-4-yl)-L-alanine;

N-[(2S)-2-mercapto-3-phenylpropionyl]-(1,1'-biphenyl-4-yl)-L-alanine;

N-(2-isopropyl-3-mercaptopropionyl)-(1,1'-biphenyl-4-yl)-L-alanine;

N-[2-mercaptomethyl-3-(3-pyridyl)propionyl]-(1,1'-biphenyl-4-yl)-L-alanine;

N-[3-(2-furyl)-2-(mercaptomethyl)propionyl]-(1,1'-biphenyl-4-yl)-L-alanine;

N-[2-mercaptomethyl-3-(3-methyl-5-isoxazolyl)propionyl]-(1,1'-biphenyl-4-yl)-L-alanine;

N-(2-isobutyl-3-mercapto-propionyl)-4-(2-thiazolyl)-L-phenylalanine;

N-[3-mercapto-2-(3-methoxyphenyl)methyl-propionyl]-4-(2-thiazolyl)-L-phenylalanine;

N-[2-(2-fluorophenyl)methyl-3-mercapto-propionyl]-4-(2-thiazolyl)-L-phenylalanine;

N-[3-mercapto-2-(2-thienyl)methyl-propionyl]-4-(2-thiazolyl)-L-phenylalanine;

N-[2-(2-furyl)methyl-3-mercapto-propionyl]-4-(2-thiazolyl)-L-phenylalanine;

N-[3-mercapto-2-(3-methyl-5-isoxazolyl)methyl-propionyl]-4-(2-thiazolyl)-L-phenylalanine;

N-[(2R)-3-mercapto-2-phenylmethylpropionyl]-4-(2-thiazolyl)-L-phenylalanine.

28. A pharmaceutical composition containing a therapeutically effective amount of N-[(2S)-3-mercapto-2-phenylmethylpropionyl]-4-(2-thiazoly)-L-phenylalanine or a salt thereof and a pharmaceutically acceptable carrier.

29. N-[(2S)-3-mercapto-2-phenylmethylpropionyl]-4-(2-thienyl)-L-phenylalanine.

30. A method for the treatment of cardiovascular disease diseases comprising administering a therapeutically effective amount of the composition of claim 28.

31. A method for the treatment of cardiovascular disease diseases comprising administering a dual ACE and NEP-inhibiting amount of the composition of claim 28.

32. A method for the treatment of cardiovascular disease diseases comprising administering an ACE-inhibiting amount of the composition of claim 28.

33. A method for the treatment of cardiovascular disease diseases comprising administering a NEP-inhibiting amount of the composition of claim 28.

* * * * *

UNITED STATES PATENT AND TRADEMARK OFFICE
CERTIFICATE OF CORRECTION

PATENT NO. : 5,994,539

DATED : November 30, 1999

INVENTOR(S) : PELLACINI, et al.

It is certified that error appears in the above-identified patent and that said Letters Patent is hereby corrected as shown below:

Title page,

Item [30], below "Jan 23, 1996 [EP] European Pat. Off. PCT/EP96/00251" insert

-- Dec. 28, 1995 [IT]   Italy ........................ MI95002773 --

Column 1, line 9, after "April 9, 1996", insert --of which applicants claim benefit under 35 USC §119(e) and a §371 application of PCT/EP96/00251, filed January 23, 1996-- .

Signed and Sealed this

Seventh Day of November, 2000

Attest:

Q. TODD DICKINSON

Attesting Officer

Director of Patents and Trademarks